US010799363B2

United States Patent
Pasini et al.

(10) Patent No.: US 10,799,363 B2
(45) Date of Patent: *Oct. 13, 2020

(54) BONE REPLACEMENT IMPLANTS WITH MECHANICALLY BIOCOMPATIBLE CELLULAR MATERIAL

(71) Applicant: THE ROYAL INSTITUTION FOR THE ADVANCEMENT OF LEARNING/MCGILL UNIVERSITY, Montreal (CA)

(72) Inventors: Damiano Pasini, Montreal (CA); Sajad Arabnejad Khanoki, Montreal (CA); Michael Tanzer, Hampstead (CA)

(73) Assignee: THE ROYAL INSTITUTION FOR THE ADVANCEMENT OF LEARNING/MCGILL UNIVERSITY, Montreal (CA)

(*) Notice: Subject to any disclaimer, the term of this patent is extended or adjusted under 35 U.S.C. 154(b) by 1654 days.

This patent is subject to a terminal disclaimer.

(21) Appl. No.: 14/310,703

(22) Filed: Jun. 20, 2014

(65) Prior Publication Data

US 2014/0363481 A1  Dec. 11, 2014

Related U.S. Application Data

(63) Continuation of application No. PCT/CA2012/001191, filed on Dec. 21, 2012.

(51) Int. Cl.
A61F 2/28 (2006.01)
A61L 27/56 (2006.01)
(Continued)

(52) U.S. Cl.
CPC .......... *A61F 2/28* (2013.01); *A61F 2/36* (2013.01); *A61L 27/56* (2013.01); *B22F 3/008* (2013.01);
(Continued)

(58) Field of Classification Search
CPC .... B22F 2999/00; B22F 3/008; B22F 3/1055; B22F 3/1103; B22F 2207/17; A61F 2/28;
(Continued)

(56) References Cited

U.S. PATENT DOCUMENTS 5,344,457 A * 9/1994 Pilliar ................. A61C 8/0012
                                                         433/174
6,993,406 B1   1/2006 Cesarano et al.
(Continued)

FOREIGN PATENT DOCUMENTS

CA  2860013   6/2013
CA  2947775   11/2015
(Continued)

OTHER PUBLICATIONS

International Search Report, PCT/CA2015/050384, dated Jul. 22, 2015.
(Continued)

*Primary Examiner* — Saif A Alhija
(74) *Attorney, Agent, or Firm* — Norton Rose Fulbright Canada

(57) ABSTRACT

A methodology integrating multiscale analysis and design optimization to design a novel bone replacement implant made of a functionally graded cellular material that meets fatigue requirements imposed by cyclic loadings. The pore microarchitecture, described by interconnectivity, porosity, pore size as well as pore topology, is optimally designed for tissue regeneration and mechanical strength. The method can contribute to the development of a new generation of bone replacement implants with a graded cellular microstructure.

19 Claims, 21 Drawing Sheets

(51) Int. Cl.
  *A61F 2/36* (2006.01)
  *B22F 3/00* (2006.01)
  *B22F 3/105* (2006.01)
  *B22F 3/11* (2006.01)
  *G06F 30/00* (2020.01)
  *G06F 30/23* (2020.01)
  *A61F 2/30* (2006.01)

(52) U.S. Cl.
  CPC .......... *B22F 3/1055* (2013.01); *B22F 3/1103* (2013.01); *G06F 30/00* (2020.01); *G06F 30/23* (2020.01); *A61F 2/3094* (2013.01); *A61F 2002/3069* (2013.01); *A61F 2002/3092* (2013.01); *A61F 2240/001* (2013.01); *A61L 2430/02* (2013.01); *B22F 3/1118* (2013.01); *B22F 2999/00* (2013.01); *Y02P 10/295* (2015.11)

(58) Field of Classification Search
  CPC .... A61F 2/36; A61F 2240/001; A61F 2/3094; A61F 2002/3092; A61F 2002/3069; G06F 17/5018; G06F 17/50; A61C 13/0004; A61L 27/56; A61L 2430/02; Y02P 10/295
  USPC .......................................................... 703/1
  See application file for complete search history.

(56) References Cited

U.S. PATENT DOCUMENTS

| | | | |
|---|---|---|---|
| 7,537,664 | B2 | 5/2009 | O'Neill et al. |
| 7,718,109 | B2 | 5/2010 | Robb et al. |
| 8,147,861 | B2 | 4/2012 | Jones et al. |
| 8,268,099 | B2 | 9/2012 | O'Neill et al. |
| 8,268,100 | B2 | 9/2012 | O'Neill et al. |
| 8,350,186 | B2 | 1/2013 | O'Neill et al. |
| 8,556,981 | B2 | 10/2013 | Jones et al. |
| 8,728,387 | B2 | 5/2014 | Jones et al. |
| 8,992,703 | B2 | 3/2015 | O'Neill et al. |
| 9,135,374 | B2 | 9/2015 | Jones et al. |
| 9,180,010 | B2 | 11/2015 | Dong et al. |
| 9,456,901 | B2 | 10/2016 | Jones et al. |
| 2006/0147332 | A1 | 7/2006 | Jones et al. |
| 2006/0276925 | A1 | 12/2006 | Lin et al. |
| 2011/0202140 | A1 | 8/2011 | Turner et al. |
| 2013/0218288 | A1 | 8/2013 | Fonte et al. |
| 2014/0363481 | A1 | 12/2014 | Pasini et al. |
| 2017/0095337 | A1 | 4/2017 | Pasini et al. |

FOREIGN PATENT DOCUMENTS

| | | | |
|---|---|---|---|
| EP | 2606859 | 6/2013 | |
| EP | 2793756 | 10/2014 | |
| EP | 3137125 | 1/2018 | |
| WO | 9933641 | 7/1999 | |
| WO | WO-9933641 A1 * | 7/1999 | ............ A61L 27/56 |
| WO | 2005051233 A2 | 6/2005 | |
| WO | 2005051233 | 11/2006 | |
| WO | 2008146141 | 12/2008 | |
| WO | 2013091085 | 6/2013 | |
| WO | 2013181375 | 12/2013 | |
| WO | 2015164982 | 11/2015 | |

OTHER PUBLICATIONS

Banhart, "Manufacture, characterisation and application of cellular metals and metal foams", Progress in Material Science 46 (2001) 559-632, 2001.

Extended European Search Report, EP 157852617, dated Dec. 6, 2017.

Lin, D., Qing, L, W., Zhou, S., and Swain, M.V. Design Optimization of Functionally Graded Dental Implant for Bone Remodelling. Composites: Part B 40 (2009) 668-675. Available online Apr. 21, 2009 (Apr. 21, 2009). Retrieved From the Internat [Retrieved Feb. 4, 2013].

Tang, C.Y., Guo, Y.Q., Tsui, C.P., and Gao, B. Multi-scale Finite Element Analysis on Biomechanical Response of Functionally Graded Dental implant / Mandible System. Journal of the Serbian Society of Computational Mechanics: vol. 1 No. 1 (2007) 164-173. Retrieved from the Internal [Retrieved Feb. 4, 2013].

Rungsiyakull, C., Li, Q., Sun, G., Li, W., and Swain, M.V. Surface Morphology Optimization for Osseointegration of Coated Implants. Biomaterials 31 (2010) 7196-7204. Available online Jun. 22, 2010 (Jun. 22, 2010). Retrieved from the Internet [Retrieved Feb. 4, 2013].

Extended European Search Report, EP 12859682.2, dated Jul. 28, 2015.

Lin, D., Qing, L., Li, W., Zhou, S., and Swain, M.V. Design Optimization of Functionally Graded Dental Implant for Bone Remodelling. Composites: Part B 40 (2009) 668-675. Available online Apr. 21, 2009 (Apr. 21, 2009). Retrieved from the Internet [Retrieved Feb. 4, 2013].

Tang, C.Y., Guo, Y.Q., Tsui, C.P., and Gao, B. Multi-scale Finite Element Analysis on Biomechanical Response of Functionally Graded Dental implant / Mandible System. Journal of the Serbian Society of Computational Mechanics: vol. 1 No. 1 (2007) 164-173. Retrieved from the Internet [Retrieved Feb. 4, 2013].

* cited by examiner

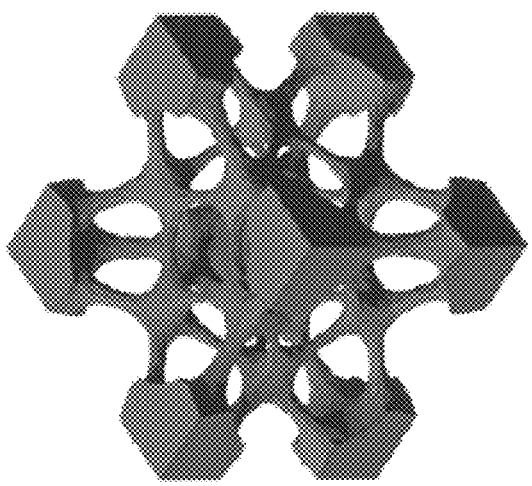
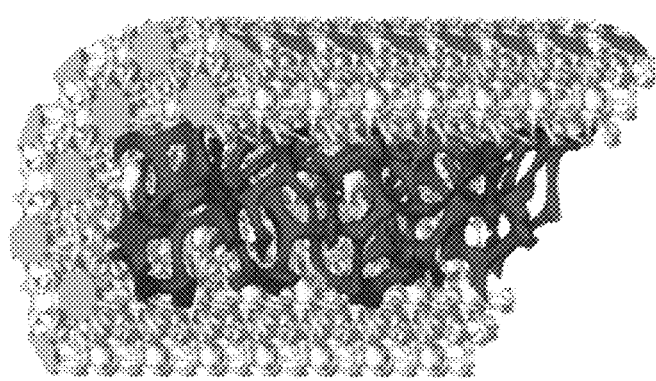
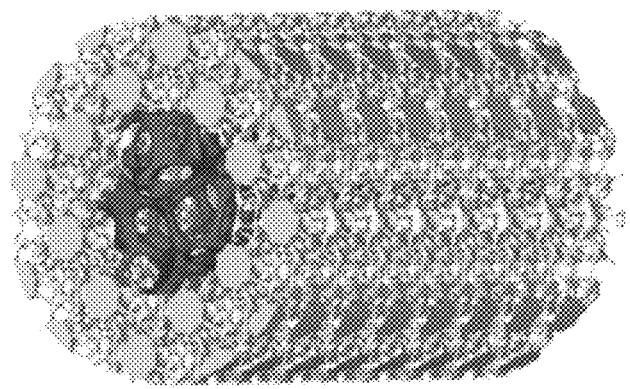
Fig-2B

Implant
Resorbed bone
Non resorbed bone

Implant
Resorbed bone
Non resorbed bone

Implant
Resorbed bone
Non resorbed bone

| Yield function | Constant |
|---|---|
| ▦ (2x2 grid) | $\left(\dfrac{\bar{\sigma}_{xx}}{\bar{\sigma}_{xx}^y}\right)^2 + 2F_{xy}^*\left(\dfrac{\bar{\sigma}_{xx}}{\bar{\sigma}_{xx}^y}\right)\left(\dfrac{\bar{\sigma}_{yy}}{\bar{\sigma}_{yy}^y}\right) + \left(\dfrac{\bar{\sigma}_{yy}}{\bar{\sigma}_{yy}^y}\right)^2 = \left(\dfrac{\bar{\tau}_{xy}}{\bar{\tau}_{xy}^y} - 1\right)^2$    $F_{xy}^* = -1.6787\rho^2 + 2.539\rho - 0.42$ |
| ✿ (hexagonal honeycomb) | $\max\left\{\dfrac{\dfrac{\bar{\sigma}_{xx}}{\bar{\sigma}_{xx}^y} - \dfrac{\bar{\sigma}_{yy}}{m_1\bar{\sigma}_{yy}^y}}{\left(1 - \left\|\dfrac{\bar{\tau}_{xy}}{\bar{\tau}_{xy}^y}\right\|^a\right)^a},\;\; \dfrac{\dfrac{\bar{\sigma}_{yy}}{\bar{\sigma}_{yy}^y} - \dfrac{\bar{\sigma}_{xx}}{m_2\bar{\sigma}_{xx}^y}}{\left(1 - \left\|\dfrac{\bar{\tau}_{xy}}{\bar{\tau}_{xy}^y}\right\|^b\right)^b}\right\} = 0$    for $\begin{cases}\rho < 0.6 \\ 0.6 < \rho < 1\end{cases}$ $\begin{aligned}a &= 16.52\rho^2 - 23.1\rho + 9.275 \\ a &= 1.5\end{aligned}$<br>for $\begin{cases}\rho < 0.6 \\ 0.6 < \rho < 1\end{cases}$ $\begin{aligned}b &= -11.61\rho^2 + 10.125\rho + 1.05 \\ b &= 3\end{aligned}$<br>for $\begin{cases}\rho < 0.6 \\ 0.6 < \rho < 1\end{cases}$ $\begin{aligned}m_1 &= 1.15e^{6.9\rho} \\ m_1 &= -205.88\rho^2 + 164.83\rho + 46.97\end{aligned}$<br>for $\begin{cases}\rho < 0.6 \\ 0.6 < \rho < 1\end{cases}$ $\begin{aligned}m_2 &= 0.305\rho^{2.35} \\ m_2 &= 0.3783\rho^{2.811}\end{aligned}$ |

Fig. 11

| | Proximal cell | Boundary cell | Proximal cell | Boundary cell |
|---|---|---|---|---|
| AH | | | | |
| FEA | | | | |
| Error ($\bar{\sigma}_{vM}$)[1] | 0.98% | 1.8% | 1.2% | 3.8% |
| Error (max($\bar{\sigma}_{vM}$))[2] | 7.1% | 8.7% | 8.2% | 18.6% |

1 - The error corresponds to the average of von Mises stress over the unit cell
2 - The error corresponds to maximum of von Mises stress over the unit cell

Fig-12

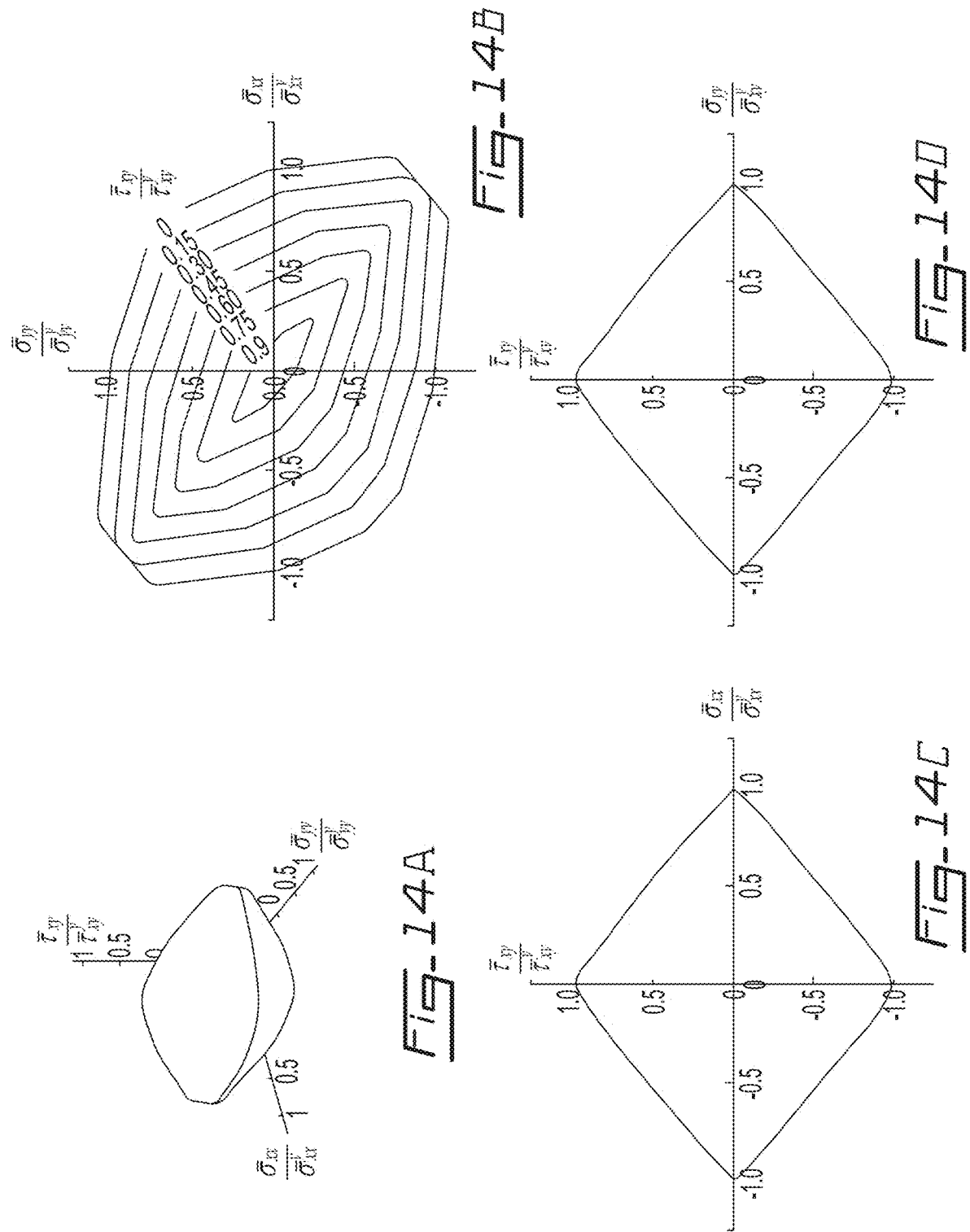

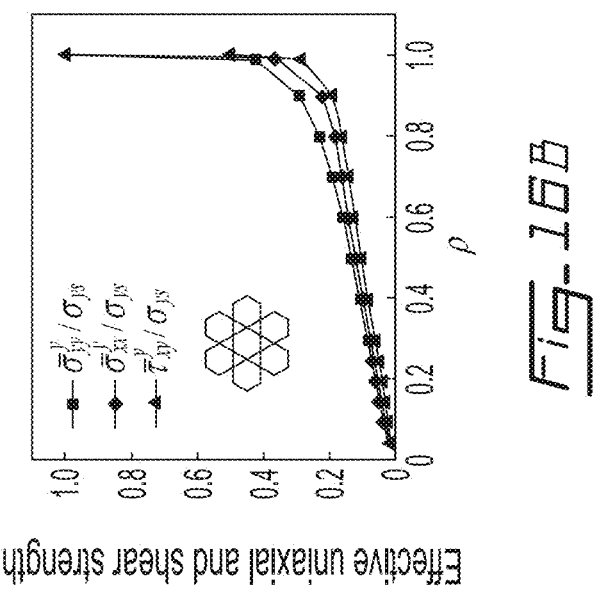
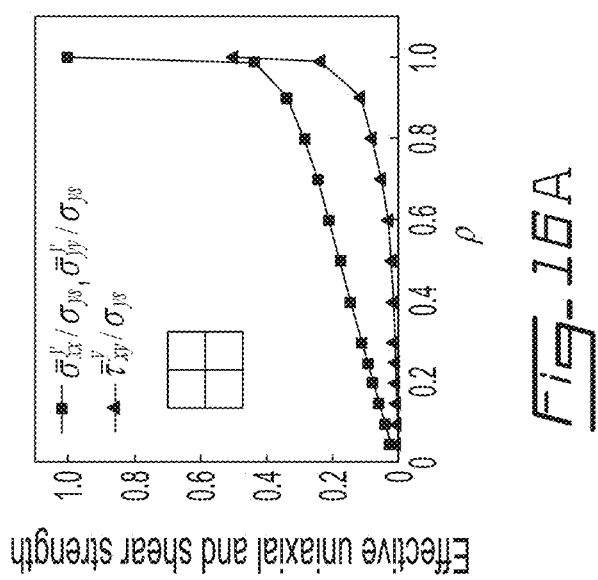
Fig. 16B
Fig. 16A

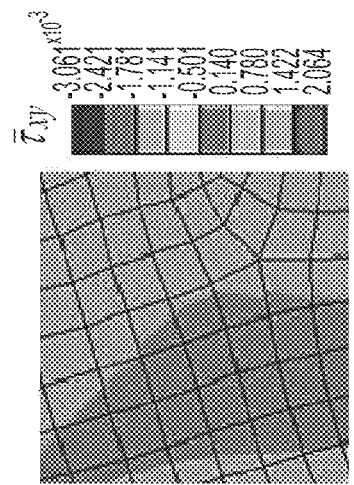
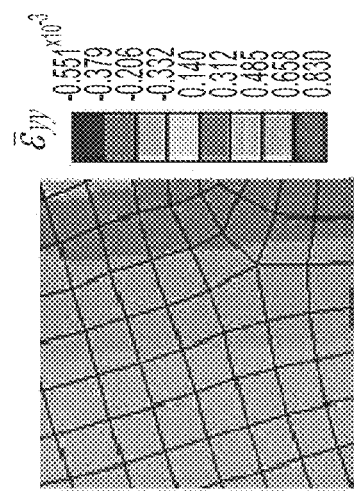
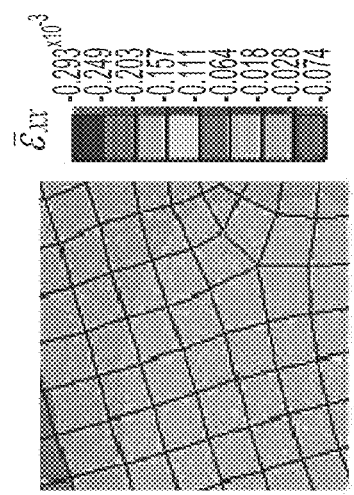
Fig-22A
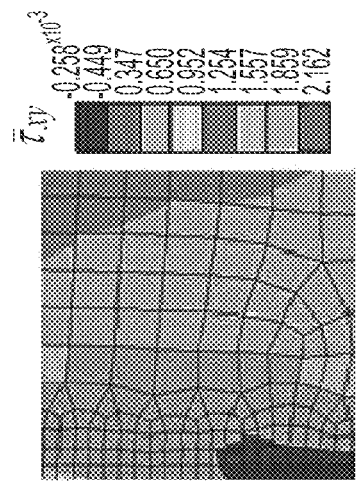
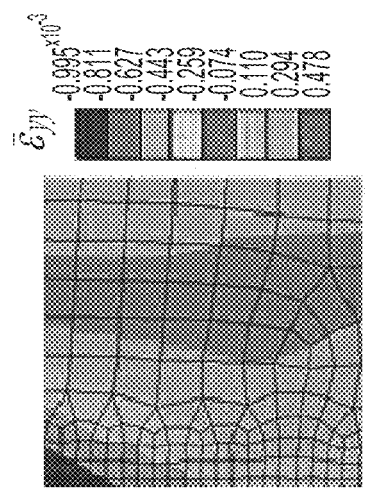
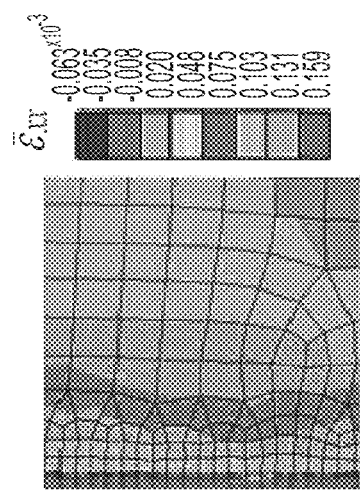
Fig-22B

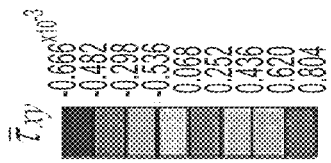
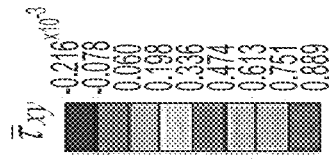
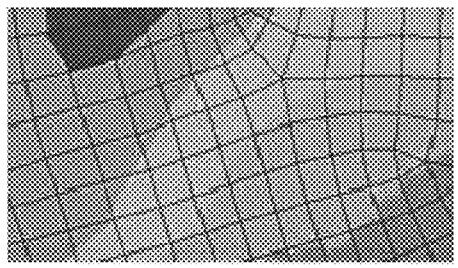
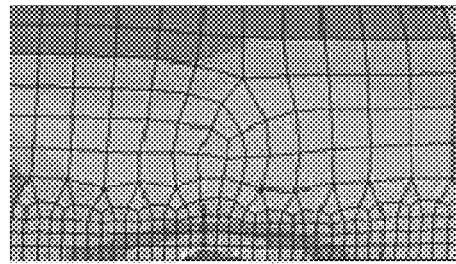
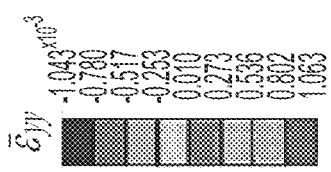
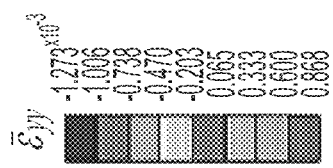
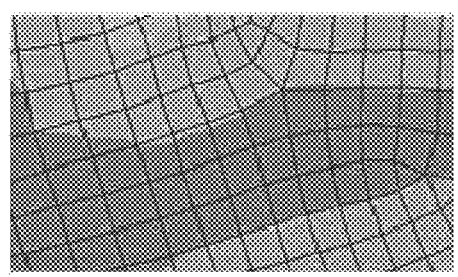
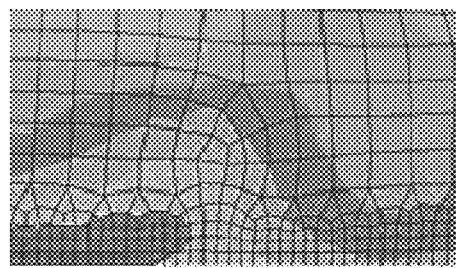
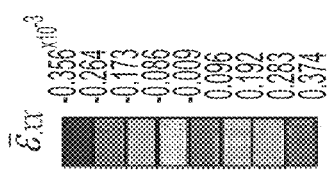
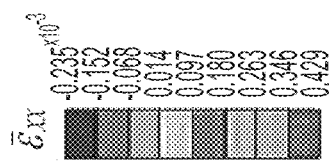
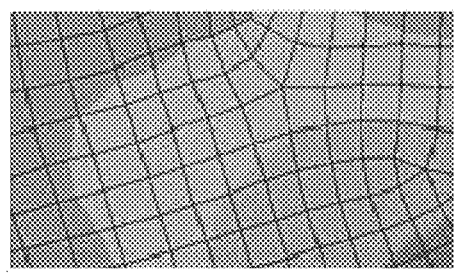
FIG-22C
FIG-22D

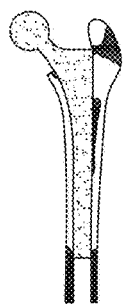
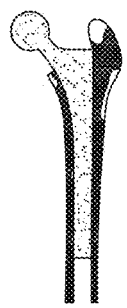
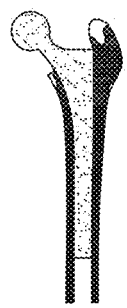
☐ Resorbed bone
■ Non resorbed bone
▨ Implant
FIG. 23A
☐ Resorbed bone
■ Non resorbed bone
▨ Implant
FIG. 23B
☐ Resorbed bone
■ Non resorbed bone
▨ Implant
FIG. 23C
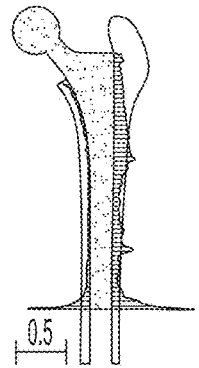
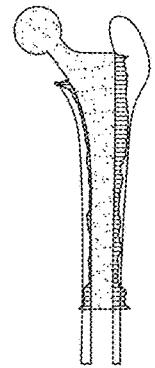
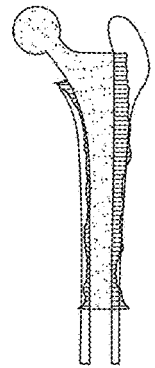
FIG. 24A
FIG. 24B
FIG. 24C
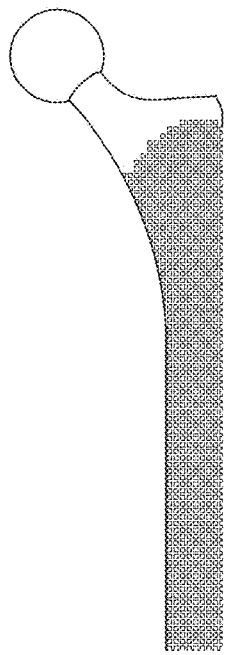
FIG. 25

BONE REPLACEMENT IMPLANTS WITH MECHANICALLY BIOCOMPATIBLE CELLULAR MATERIAL

CROSS-REFERENCE TO RELATED APPLICATIONS

This application is a continuation of International Patent Application No. PCT/CA2012/001191 filed Dec. 21, 2012 which claims priority on U.S. Provisional Application No. 61/579,758 filed Dec. 23, 2011, the contents of both of which are incorporated herein by reference.

TECHNICAL FIELD

The present disclosure relates to the field of orthopaedic implants, and more particularly to methods and systems for designing orthopaedic implants, as well as the implants themselves produced in accordance with such design methods.

BACKGROUND

Revision surgeries of total hip arthroplasty are often caused by a deficient mechanical biocompatibility of the implant. Mechanical biocompatibility is a general term that refers to the ability of the implant to harmonize its mechanical properties with those of the host bone. Two main culprits, among others, for revision surgery are bone-implant interface instability and bone resorption.

Current orthopedic prostheses are generally made of uniform density, homogenous material such as 316L stainless steel, cobalt chromium alloys, titanium-based alloys and tantalum. Over the last few decades, the design of the orthopedic prostheses has been improved to achieve long-term fixation and easy osseointegration. Although technological advances have made current total hip arthroplasty successful, over 13% of the hip prostheses still require revision surgeries as a result of bone resorption and aseptic loosening of the implant (Kurtz et al., 2007). Revision surgery is a much more complex procedure than the first total hip arthroplasty (THA) due to bone degradation around the first implant. Bone degradation compromises bone ability to adequately secure the new implant.

Although patient-related factors, such as sickle cell anaemia (Vichinsky et al., 1999), poor bone quality (Kobayashi et al., 2000), and high body mass index may predispose the patient to prosthetic failures, mechanical rather than medical factors are major causes of implant failure (Kowalcyk, 2001).

Current orthopaedic implants are generally stiffer than the bone adjacent to the prosthesis. Due to its stiffness, an implant prevents the applied stress from being transferred to the adjacent bone, thereby resulting in bone resorption around the implant. This weakens the implant support, which leads to bone fracture and implant loosening. Over the last three decades, alternative implant designs have been proposed to reduce stress shielding and minimize the associated clinical consequences (Glassman et al., 2006). Recent implant designs have only been partially successful, as the solution of one problem has given rise to another one. For example, to overcome the mismatch between a stiff stem and the adjacent bone, composite and isoelastic hip stems were introduced (Adam et al., 2002; Trebse et al., 2005). The results of these studies showed an undesired increase of the shear stress between the implant and the bone, an outcome that increases the risk of interface motion (Harvey et al., 1999; Huiskes et al., 1992). These attempts help elucidate the conflicting nature of stress shielding and bone-implant interface stability, which remain a major challenge.

The conflict existing between stress shielding and interface shear stress have been identified in the seminal work of Kuiper and Huiskes (1992; 1997), who attempted to find a trade off design of a bidimensional hip implant. They showed that one solution to this issue is an implant whose material properties vary locally throughout the structure. A non-homogeneous distribution of elastic properties within the hip stem could contribute to minimizing the probability of interface failure while concurrently limiting the amount of bone loss. In their approach, however, the solution of the multi-objective problem has been simplified, reformulated and solved with a single objective optimization strategy. As a result the whole set of trade-off designs could not have been captured. Hedia et al. (2006; 2004) attempted to reconcile the conflicting nature of these objective functions by proposing to use three bioactive materials: hydroxyapatite, bioglass, and collagen, to design a graded cementless hip stem. Although their implant design reduced bone resorption and bone-implant interface stresses, the use of such bioactive materials have limitations due to their brittleness and insufficient strength when applied to load-bearing applications (Watari et al., 1997; Katti, 2004; Thompson and Hench, 1998). In a more recent study, Fraldi et al. (2010) applied a maximum stiffness topological optimization strategy to re-design a hip prostheses with the goal of reducing stress shielding in the femur. According to this method, elements with intermediate volume fraction (between 0 and 1) are penalized to limit their presence in the final solution. For regions with intermediate relative density, certain microstructures should be proposed to match those materials in terms of effective elastic properties. Laser micro-drilling is suggested to create the required micro-porosity, an option that can be used only on the implant surface, not throughout the implant.

Other advances in total hip replacement have used a microstructural material over a fully dense material. Hip implants with porous tantalum have been proposed in knee and hip replacement surgery (Bobyn et al., 2004). Tantalum foam is an excellent material due to its biocompatibility, high volumetric porosity, and modulus of elasticity similar to that of bone. To create the tantalum foam, pure tantalum is chemically deposited on a carbon skeleton. Consequently, the microstructure of a tantalum foam implant has an almost uniform and random distribution of pore shape and size (Bobyn et al., 2004) throughout the implant. These material characteristics, however, have been demonstrated incapable of solving the conflicting nature of the physiological phenomena occurring in an implant (Kuiper and Huiskes, 1992; 1997). Whereas the reduced stiffness of the foam decreases bone resorption, the uniform distribution of cells has the undesired effect of increasing the interface stresses.

Therefore, there is a need for improved methods and systems for designing orthopaedic implants, and for improved implants designed by such methods.

SUMMARY

According to a broad aspect of the present invention there is provided a graded cellular implant for bone replacement having a non-homogeneous distribution of material properties. The bone replacement implant is defined by a plurality of unit cells. Each unit cell has a lattice microstructure and a cell topology, either closed and/or open as well as a pore geometry. The pore geometry is defined by pore size, pore shape and wall thickness. The cell topology is optimized to ease mass transport conditions that influence cell phenotype, tissue ingrowth, and nutrient settings, as well as exhibiting a predetermined density pattern in the bone implant that is obtained to minimize bone loss and interface failure when implanted.

In accordance with a first aspect, there is provided a method for designing a graded cellular bone implant having non-homogeneous distribution of material properties comprising the steps of: generating a finite element model of the implant comprising a plurality of unit cells defining a lattice microstructure; calculating a homogenized stiffness tensor for each unit cell; determining a homogenous medium for each unit cell having an equivalent homogenized stiffness tensor; determining the average macroscopic strains and stresses on the implant using the homogenized stiffness tensors by conducting a finite element analysis; generating a microscopic stress field for each unit cell using a stress recovery procedure conducted on the determined macroscopic strains and stresses; determining if the microscopic stress field of each unit cell is below a predefined failure criterion, and if so, performing a multiobjective optimization to minimize bone loss and interface failure by optimizing at least one constraint including average porosity, mean pore size and cell wall thickness for each unit cell; generating a model of the graded cellular bone implant combining the optimized microscopic stress field of each unit cell.

There is also provided a method for producing a prosthetic graded cellular bone implant having non-homogeneous distribution of material properties comprising the steps of: generating a finite element model of the implant comprising a plurality of unit cells defining a lattice microstructure; calculating a homogenized stiffness tensor for each unit cell; determining a homogenous medium for each unit cell having an equivalent homogenized stiffness tensor; determining the average macroscopic strains and stresses on the implant using the homogenized stiffness tensors by conducting a finite element analysis; generating a microscopic stress field for each unit cell using a stress recovery procedure conducted on the determined macroscopic strains and stresses; determining if the microscopic stress field of each unit cell is below a predefined failure criterion, and if so, performing a multiobjective optimization to minimize bone loss and interface failure by optimizing at least one constraint including average porosity, mean pore size and cell wall thickness for each unit cell; generating a model of the graded cellular implant combining the optimized microscopic stress field of each unit cell; and producing the prosthetic graded cellular bone implant from the model of the graded cellular implant.

In an embodiment, the bone implant is a hip implant, a knee implant, an elbow implant, a shoulder implant, a wrist implant, an ankle implant or a dental implant. In another embodiment, the porosity of the implant is greater than or equal to 40%. In a further embodiment, the mean pore size of the implant is between 50 μm and 800 μm. In another embodiment, the cell wall thickness of each unit cell is between 70 μm and 100 μm.

BRIEF DESCRIPTION OF THE DRAWINGS

Reference will now be made to the accompanying drawings.

FIG. 2(b) illustrates the conceptual design for graded cellular bone implant according to an embodiment wherein a three-dimensional view (a), a three-dimensional half-section (b), and a cellular bone element (c) are viewed.

FIG. 11 is a mathematical table of the yield surfaces as a function of relative density for square and Kagome unit cells.

FIG. 12 is a table illustrating the comparison of microscopic stress distribution obtained by detailed FEA an AH for the unit cells located at the proximal region and closed to the implant border.

FIGS. 14(a) to (d) illustrate the yield surface of a square cell topology under combined multiaxial macroscopic stress state ($\bar{\sigma}_{xx}$, $\bar{\sigma}_{yy}$, and $\bar{\tau}_{xy}$) for a relative density ρ=50%.

FIGS. 16(a) and (b) are graphs of the yield strength as a function of relative density for (a) square and (b) Kagome.

FIGS. 22(a) to (d) are graphs of the macroscopic strain distribution (solution B in FIGS. 19(a) and 19(b)) as a result of load case 1 at (a) the proximal part and (b) the border of the square lattice implant, and (c) the proximal part and (d) the border of the Kagome lattice implant.

FIGS. 23(a) to (c) are section views illustrating distribution of bone resorption around (a) fully dense titanium implant, (b) graded cellular implant with square topology (solution B) in FIG. 19(a), (c) graded cellular implant with Kagome topology (solution B in FIG. 19(b).

FIGS. 24(a) to (c) are section views illustrating distribution of local shear interface failure $f(\sigma)$ around (a) fully dense titanium implant, (b) graded cellular implant with square topology (solution B in FIG. 19(a), (c) graded cellular implant with Kagome topology (solution B in FIG. 19(b).

FIG. 25 is a side view of a prototype hip bone implant polypropylene proof-of-concept of the cellular implant (solution B in FIG. 19(a).

It will be noted that throughout the appended drawings, like features are identified by like reference numerals.

DETAILED DESCRIPTION

Figure 1:
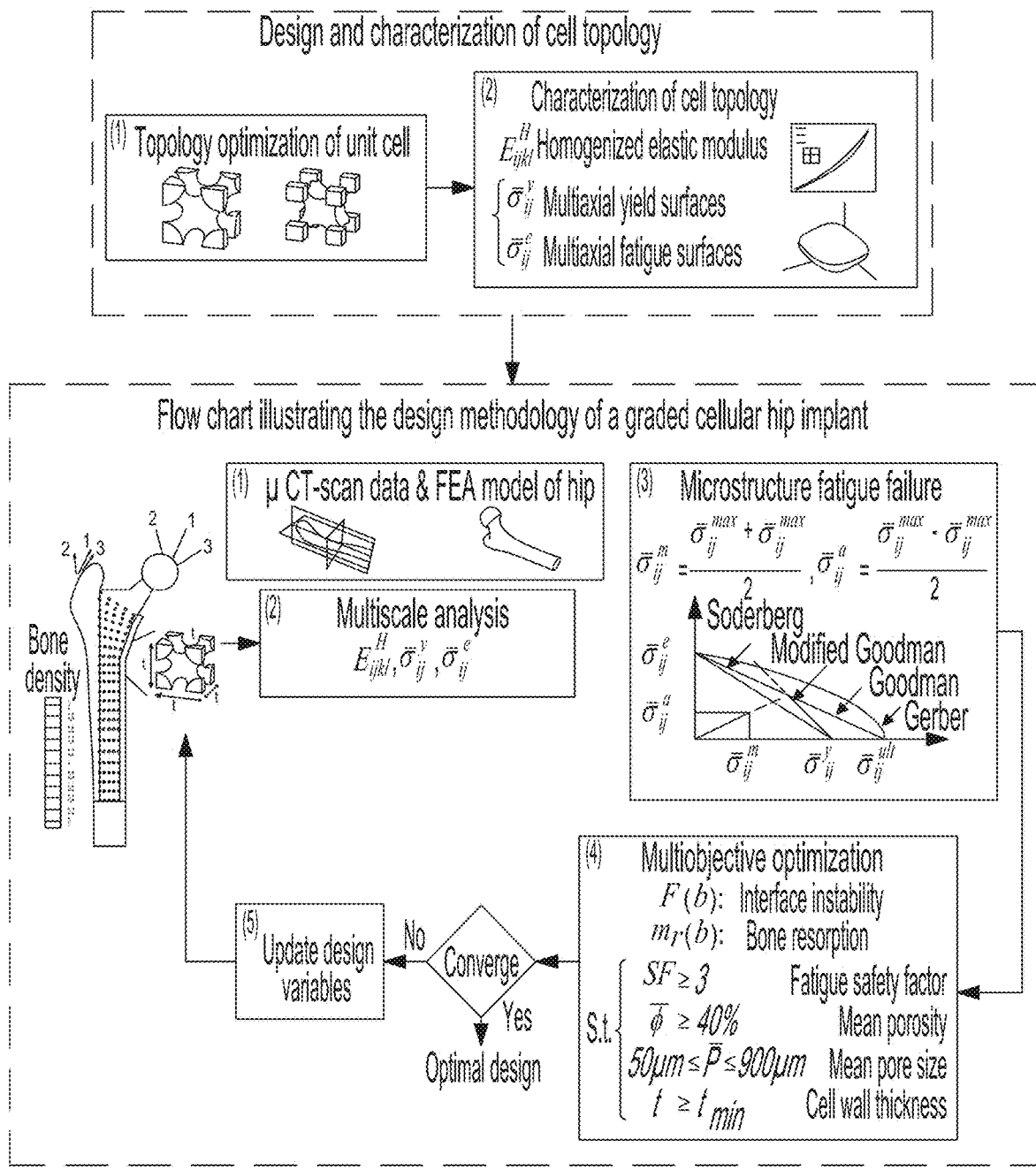
FIG. 1 is a flow chart in block diagram form illustrating the design methodology for the cell topology and the graded cellular hip implant including the fatigue analysis of the lattice material

Referring to FIG. 1, the methodology to design a functionally graded cellular implant hip with a lattice microarchitecture that meets the requirements for bone tissue regeneration and mechanical strength is shown. It consists of three parts, described in sequence in the subsequent sections. The first addresses the search for an optimum cell topology, which satisfies the requirements for a successful bone tissue engineering scaffold. This step is illustrated in the upper box of FIG. 1. The other two, depicted together in the box below, pertain to the design of the lattice material for static and fatigue failure.

The requirements for bone tissue regeneration that are account for in the present methodology include good osteoconductivity, high porosity to facilitate transport of nutrients and metabolic wastes, sufficient mechanical strength to support physiological loading conditions, and appropriate biodegradability (Kang et al., 2010; Hollister, 2005). These attributes are controlled by the pore microarchitecture, in particular by interconnectivity, porosity, pore size as well as pore topology. Pore topology describes geometric properties independent of cell size and shape, as well as invariant to stretching, bending and twisting. The cell architecture affects functional characteristics such as elastic modulus, permeability, and diffusivity (Chu et al., 2002). The latter describes mass transport conditions that in turn influence cell phenotype, tissue ingrowth, and nutrient settings. The functions of mechanical support and tissue formation are antagonist. For example, while increased porosity and pore size facilitate bone ingrowth, larger pores might weaken the scaffold integrity and thus reduce its mechanical properties. In addition, a match of the elastic modulus of the scaffold to that of the host bone has the undesired effect of penalizing the diffusivity and permeability of the scaffold, which need to be maximized for better cell migration and biological transport (Kang et al., 2010; Hollister, 2005). Hence the method proposed here solves the challenge of finding trade-off solutions of the pore geometries. We use multiobjective topology optimization to create cell architectures with improved fatigue properties, high vascularization and direct osteogenesis, superior osteochondral ossification (Kang et al., 2010; Hollister, 2005; Lin et al., 2004). For the aspects of fatigue, i.e. to maximize fatigue resistance, we resort to our recently developed method to create cells with smooth shape (Abad et al., 2012).

It is provided a novel type of implant, which in contrast to current known implants made of either a fully solid or a foam material, consists of a lattice microstructure with non-homogeneous distribution of material properties. A methodology based on multiscale mechanics and design optimization is introduced to synthesize a graded cellular implant that can minimize concurrently bone resorption and implant interface failure.

It is thus hereby disclosed a methodology integrating multiscale analysis and design optimization to design a novel implant made of graded cellular material. The method can contribute to the development of a new generation of orthopaedic implants with a graded cellular microstructure that will reduce the clinical consequences of current implants.

The procedure is applied to the design of a 2D left implanted femur with optimized gradients of relative density. The optimized cellular implant is compared to a fully dense titanium implant and a homogeneous foam implant with a relative density of 50%. The bone resorption and the maximum value of interface stress of the cellular implant is found to be over 70% and 50% less than the titanium implant while being 53% and 65% less than the foam implant. Finally, a proof-of-concept of the graded cellular implant was fabricated by using rapid prototyping to assess the manufacturability of the design.

As explained hereinbelow, a homogenization method was reviewed and is used to capture the mechanics of the implant at the micro and macro scale. A multiobjective optimization is also been applied to find optimum gradients of material distribution that minimizes concurrently bone resorption and bone-implant interface stresses. The results have shown that the optimized cellular implant exhibits a reduction of 76% of bone resorption and 50% of interface stress, with respect to a fully dense titanium implant.

Excluding biocompatibility requirements, three other requirements are identified as indicators of implant success which need to be considered in the design of THA implants. These requirements include (i) implant stability in the short and long term, (ii) preservation of bone tissue around the implant from resorption, and (iii) high wear and corrosion resistance of the articulating surfaces. The volumetric amount of wear particle and its clinical consequences have been reduced considerably by the development of extremely wear resistance polymers (Moen et al., 2011; Kurtz et al., 2011) or the design of metal-on-metal implants (Grübl et al., 2007; Neumann et al., 2010). Nevertheless, the reduction of bone-implant interface instability and bone resorption in the long term still remained a challenge for implant success.

Recent advances in additive manufacturing, such as Electron-Beam Melting (EBM), Selective Laser Melting (SLM), Stereolithography Apparatus (SLA), and other rapid prototyping techniques, offer the possibility of novel bone-replacement implants with a controlled cellular microstructure (Parthasarathy et al., 2010; Heinl et al., 2008; Stamp et al., 2009; Yang et al., 2002; Murr et al., 2010). As a result, cellular components with tailored microstructures can be built with a high level of quality, accuracy and reliability. Besides providing an exceptional degree of control over the mechanical properties, such manufacturing processes are capable of building graded cellular structures. As demonstrated by the work of Kuiper and Huiskes (1992; 1997) this feature is an asset for bone-replacement implants since the internal skeleton of the prosthesis can be designed to ease osseointegration as well as to match the local mechanical properties of the femoral bone. By properly selecting topology, size, and relative density of the unit cell of the implant, it is thus possible to: (a) fabricate implants which can provide mechanical properties mimicking those of the host bone; (b) manufacture three-dimensional structures with an interconnected porosity and pore sizes suitable to bone ingrowth and vascularization; and (c) customize implants for each patient by using CT scan data of the patient's bone.

The present disclosure proposes a systematic methodology for the design of bone-replacement implants with improved structural stability. For total hip arthroplasty for example, but not limited to, an implant design with tailored gradients of lattice material that can simultaneously minimize bone resorption and bone-implant interface stress is disclosed. The procedure that hinges on multiscale mechanics theory and multiobjective optimization is applied to the design of a bidimensional femoral hip implant with optimal graded cellular microstructure. Its biocompatibility performance is discussed herein.

Kuiper and Huiskes (1992; 1997) showed that the use of a graded material in an orthopaedic stem can lead to a reduction of both stress shielding and bone-implant interface stress. To this end, hierarchical computational procedure (Coelho et al., 2008; Rodrigues et al., 2002; Gonçalves et al., 2011; Coelho et al, 2011) can be implemented to design an optimum material distribution within the implant. This strategy might generally require a high computational cost besides yielding a microstructure which is difficult to fabricate.

It is disclosed herein a design of gradients of material properties through a tailored lattice microstructure, whose geometrical parameters are optimized in each region of the implant to achieve minimum bone loss and implant interface failure.

The mechanical properties of a cellular structure depends on the relative density and the geometric parameters of the unit cell, as described, for example, by the expression of the Young's modulus:

$$E^* = CE_s \left(\frac{\rho}{\rho_s}\right)^m \quad (1)$$

where $E^*$ is the effective Young's modulus of the unit cell, $\rho$ is the density of the unit cell, and $E_s$ and $\rho_s$ are the Young's modulus and density of the constitutive material, respectively. m has a value varying from 1 to 3 as determined by the mechanical failure mode of the unit cell, and C is a geometric constant of the unit cell. By changing the relative density of the lattice microstructure, it is thus possible to obtain desired values of mechanical properties in any zone of the implant.

Figure 2A:
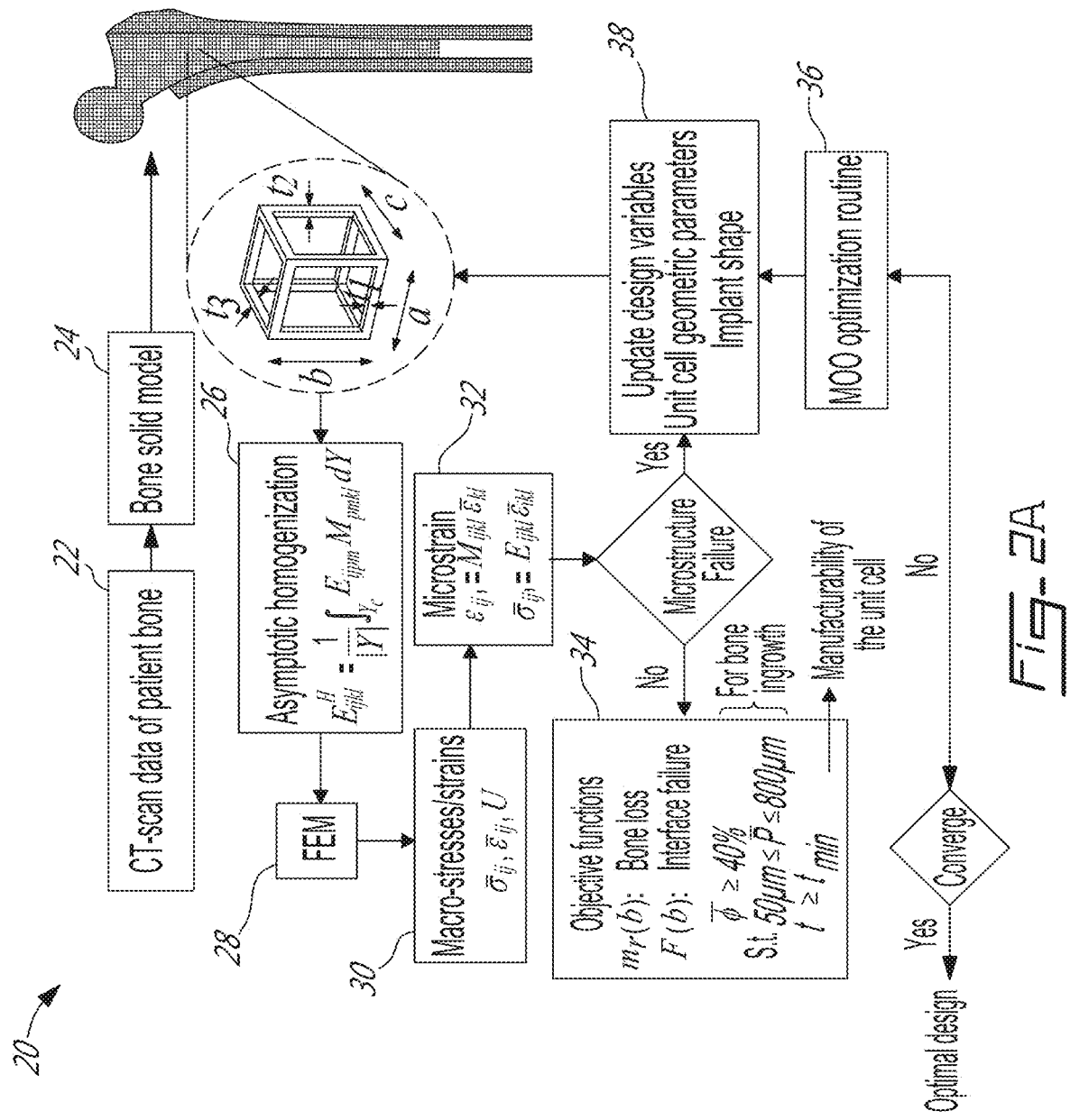
FIG. 2(a) illustrates a flow chart illustrating the design of a graded cellular hip implant minimizing bone resorption and implant interface failure, in accordance with an embodiment.

FIG. 2 summarizes the procedure 20 proposed here to design a cellular implant with controlled gradients of mechanical properties. The method 20 integrates a multiscale mechanics approach to deal with the scale-dependent material structure and a multiobjective optimization strategy to handle the conflicting nature of bone resorption and implant interface failure. The main steps identified by the numbers reported in the flow chart of FIG. 2 are described hereinbelow.

The first step 22 consists in processing CT-scan data of a patient bone to generate 24 a finite element model of the bone. The design domain of the prosthesis is assumed to possess a 3D lattice microstructure, where the unit cell, i.e. the building block, can be of any arbitrary topology (FIG. 2). The microscopic parameters of the unit cell geometry and the macroscopic shape of the implant are the design variables of the vector b. The unit cell is assumed to be locally periodic, and its field quantities, such as stress and strain, to vary smoothly through the implant. The characteristic length of the unit cell in the cellular implant is assumed to be much smaller than the characteristic length of the macro dimensions of the implant. Hence, the microstructure is replaced 26 with a homogeneous medium whose equivalent mechanical properties, in particular the homogenized stiffness tensor of each unit cell, are calculated through the asymptotic homogenization theory (Guedes et al., 1990; Hassani and Hinton, 1998; Fang et al., 2005; Zienkiewicz and Taylor, 2005).

The homogenized stiffness tensors are then used to construct the stiffness matrix which will be the input to the Finite Element (FE) solver 28. As a result, the average strains and stresses throughout the bone and the structure of the prosthesis are calculated 30.

To obtain the microscopic stress field for each unit cell from the macroscopic strain, a stress recovery procedure is used 32. If the microscopic stress level is below a predefined failure criterion, the macroscopic stresses and strains representing the mechanical behavior of the implant are used to evaluate bone loss ($m_r(b)$) and interface failure (F(b)) 34. In the formulation of the multiobjective optimization problem, the constraints are set on the average porosity of the cellular implant $\bar{\phi}(b)$, the mean pore size $\bar{P}$, and the minimum thickness of cell walls $t_{min}$. In particular, $\bar{\phi}(b)$ 40% and 50 µm≤$\bar{P}$≤800 µm are selected to ease bone ingrowth [41, 42]. The thickness of the cell walls is selected to be greater than the minimum resolution $t_{min}$ offered by a given manufacturing process. For example, $t_{min}$ is 100 µm and 70 µm respectively for SLM and SLA (Yang et al., 2002; Wang, 2005). If the solutions of the optimization have not converged, then the vector b of the design variables is updated to find the set of non-dominated solutions of the Pareto front (36, 38). If the unit cell fails at microscale level, the cell walls will be iteratively increased to reduce the microscopic stresses 38.

As described above, multiscale mechanics and multiobjective optimization are integrated aspects of the method 20 proposed herein.

Figure 3:
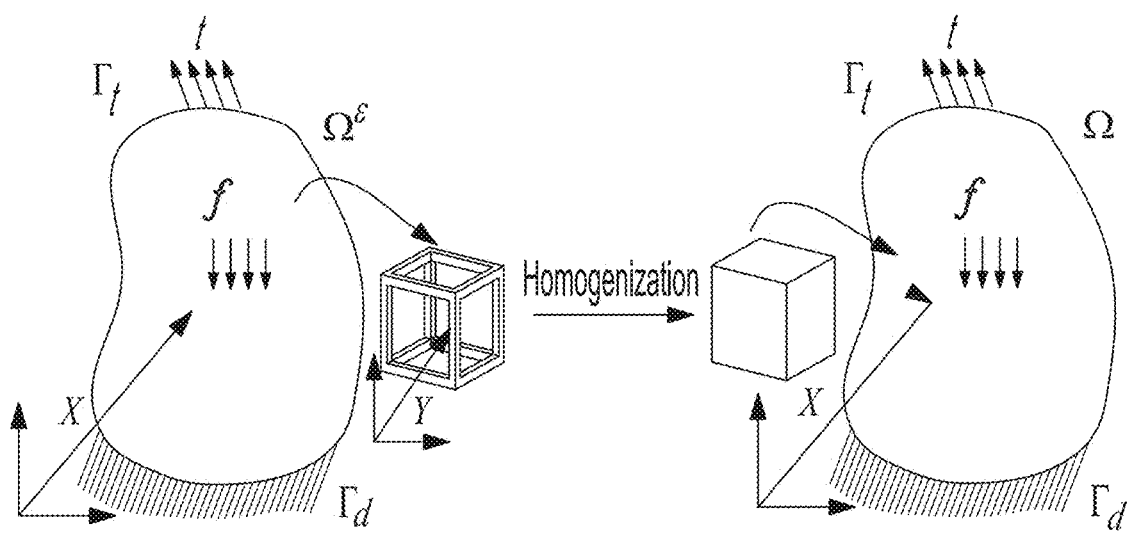
FIG. 3 illustrates the homogenization concept of a cellular structure.

The deformation and failure mechanisms of a structure with heterogeneous material can occur at both the macroscopic and microscopic scales. In a full scale simulation, the heterogeneities are explicitly modeled at the microscale to guarantee high accuracy. The computational effort, however, can be very lengthy and time-consuming. As an alternative, the microstructure can be replaced by a homogeneous medium, and the mathematical theory of homogenization can be used to characterize the mechanical behavior of heterogeneous media. As shown in FIG. 3, a body $\Omega^\varepsilon$ with a periodic microstructure subjected to the traction t at the traction boundary $\Gamma_t$, a displacement d at the displacement boundary $\Gamma_d$, and a body force f can be replaced by a homogenized body $\Omega$ with the prescribed external and traction boundaries applied to $\omega^\varepsilon$, without geometrical details and voids of the local coordinate system.

In an embodiment, the homogenized properties and strength of a cellular structure can be obtained by performing either analytical or numerical or experimental approaches. Extensive efforts have been devoted to the derivation of the equivalent mechanical properties by structural analysis (Gibson and Ashby, 1999; Masters and Evans, 1996; Christensen, 2000; Wang and McDowell, 2004; Kumar and McDowell, 2004; Warren and Byskov, 2002; Chen and Huang, 1998). In these studies, the effective moduli and yield strength of a cellular material are generally modeled by assuming that the cell walls flex like beams. Despite the simplicity of this method in calculating the overall mechanical properties, the results are reliable only if the relative density is lower than 0.3 (Wang and Mcdowell, 2004). Furthermore, the actual stress distribution within the unit cell walls cannot be captured.

In another embodiment, and as an alternative method, the asymptotic homogenization method is used in this work to deal with the multiscale analysis of the cellular implant. This technique is applied to calculate the homogeneous stiffness matrix of the unit cell for different values of relative density as well as to determine the microscopic stresses and strains (Guedes and Kituchi, 1990; Zienkiewicz and Taylor, 2005; Hollister and Kikuchi, 1992). The asymptotic homogenization method has been widely used in topology optimization (Bendsøe and Sigmund, 2003; Hassani and Hinton, 1998; Díaaz and Kikuchi, 1992; Suzuki and Kikuchi, 1991; Bendsøe and Kikuchi, 1988) and hierarchical design of materials and structures (Coelho et al., 2008; Rodrigues et al., 2002; Gonçalves Coelho et al., 2011; Coelho et al., 2011). In this work, unlike hierarchical topology optimization, a pre-defined unit cell topology with parametric geometry is considered as the microstructure of the implant; then, the optimization algorithm searches for the optimum unit cell geometry of the lattice to minimize the antagonist objective functions under a set of constraints. This procedure is similar to the one developed by Bendsøe and Kikuchi (1988) and is not limited to any cell topology.

The approach of the asymptotic homogenization technique and calculating effective stiffness and microscopic stress and strain assumes that each field quantity depends on two different scales: one on the macroscopic level x, and the other on the microscopic level, y=x/ε, where a is a magnification factor that enlarges the dimensions of a unit cell to make it comparable with the dimensions of the material. The field quantities, such as displacement, stress, and strain, are assumed to vary smoothly at the macroscopic level, being periodic at the microscale. The effective properties of the periodic material are determined through the solution of local problems formulated on the representative volume element (RVE) of the material. As a result, the homogenized stiffness tensor $(E_{ijkl}^{H})$ of a cellular material may be defined as follow:

$$E_{ijkl} = \frac{1}{|Y|} \int_{Y_C} E_{ijpm} M_{pmkl} dY \qquad (2)$$

where |Y| is the volume of the entire unit cell with void, $Y_c$ is the solid part of the cell, $E_{ijkl}$ is the local elasticity tensor that depends on the position within the representative volume element, i.e. $E_{ijkl}$ is equal to the elasticity tensor of the material located in the cell walls and it vanishes in the voids. $M_{ijkl}$ is the local structure tensor, which relates the macroscopic strains $(\bar{\varepsilon})$ to the local or microstructural strains $(\varepsilon)$ through the relation:

$$\varepsilon_{ij} = M_{ijkl}\bar{\varepsilon}_{ij}, \quad M_{ijkl} = \frac{1}{2}(\delta_{ik}\delta_{jl} + \delta_{il}\delta_{jk}) - \varepsilon_{ij}^{*kl} \qquad (3a, b)$$

where $\delta_{ij}$ is the Kronecker delta, and $\varepsilon_{ij}^{*kl}$ is the microstructural strain corresponding to the component kl of macroscopic strain tensor $(\bar{\varepsilon}_{kl})$. $\varepsilon_{ij}^{*kl}$ is the solution of the following equation:

$$\int_{Y_C} E_{ijpm}\varepsilon_{ij}^{1}(v)\varepsilon_{pm}^{*kl}(u)dY = \int_{Y_C} E_{ijkl}\varepsilon_{ij}^{1}(v)\bar{\varepsilon}_{kl}dY \qquad (4)$$

where $\varepsilon_{ij}^{1}(v)$ is the virtual strain. In general, $\bar{\varepsilon}_{kl}$ can be an arbitrary macroscopic strain tensor. Considering the assumption of small deformation and linear material behavior, $\bar{\varepsilon}_{kl}$ may be written as a linear combination of unit strains. For a two-dimensional case, the unit strains are defined as:

$$\bar{\varepsilon}_{11}=[1\ 0\ 0]^T, \bar{\varepsilon}_{22}=[0\ 1\ 0]^T,$$

$$\bar{\varepsilon}_{12}=[0\ 0\ 1]^T \qquad (5)$$

To calculate the effective mechanical properties of a cellular material, the first task is to obtain the matrix $M_{ijkl}$. After discretizing the RVE domain, the unit strains are applied to each element of the FE model. Periodicity of the strain field is ensured by imposing periodic boundary conditions on the RVE edges. The direct method is selected to derive periodic boundary conditions. The microscopic strain field $(\varepsilon_{ij}^{*kl})$ inside the RVE is obtained by solving Eq. (4). The results are substituted into Eq. (3b) to calculate the local structure tensor $M_{ijkl}$ for each element of the RVE. Finally, the effective stiffness tensor $E_{ijkl}^{H}$ is obtained by calculating Eq. (2). Once the local structure tensor, $M_{ijkl}$, is obtained, the microscopic strains and stresses corresponding to the macroscopic strain can be obtained via Eq. (3a) and the constitutive equation of cell wall material.

The steps described above are used to compute the homogenized stiffness tensor for each unit cell of the cellular hip implant (FIG. 2). These tensors are used to construct the global stiffness matrix for the FE solver to obtain macroscopic stress and strain distribution within bone and implant. The values are then postprocessed to evaluate the objective functions of the multiobjective optimization problem.

For the design of an optimum implant, the simultaneous minimization of the amount of bone loss around the prosthesis is imposed, and the probability of mechanical failure at the bone-implant interface. As illustrated in FIG. 2, the multiobjective optimization problem can be formulated as:

$$\text{Minimize} \begin{cases} m_r(b) & \text{bone loss} \\ F(b) & \text{interface failure} \end{cases} \qquad (6)$$

Subject to  $\bar{\phi}(b) \geq 40\%$      average porosity $50\ \mu m \leq \bar{P} \leq 800\ \mu m$    mean pore size $t \geq t_{min}$               cell wall thickness The amount of bone loss around the stem is determined by assessing the amount of bone that is underloaded. Bone can be considered locally underloaded when its local strain energy $(U_i)$ per unit of bone mass $(\rho)$, averaged over n loading cases $$\left( S = \frac{1}{n}\sum_{i=1}^{n}\frac{U_i}{\rho} \right),$$

is beneath the local reference value $S_{ref}$, which is the value of S when no prosthesis is present. However, it has been observed that not all the underloading leads to resorption, and a certain fraction of underloading (the threshold level or dead zone s) is tolerated. Indeed, bone resorption starts when the local value of S is beneath the value of $(1-s)S_{ref}$. Using this definition, the resorbed bone mass fraction m, can be obtained from:

$$m_r(b) = \frac{1}{M} \int_V g(S(b)) \rho dV \qquad (7)$$

where M and V are the original bone mass and volume respectively, and g(S(b)) is a resorptive function equal to unity if the local value of S is beneath the local value of $(1-s)S_{ref}$ and equal to 0 if $(1-s)S_{ref}<S$. In this study, the value of dead zone s is assumed to be 0.5. The other objective is to minimize the probability of interface failure, which is expressed by the following functional of the interface stress distribution:

$$F(b) = \frac{1}{n} \sum_{i=1}^{n} \int_{\Pi} f(\sigma_i^b) d\Pi \qquad (8)$$

where F(b) is the global interface function index, $\sigma_i^b$ is the interface stress at the loading case i, depending on the design variable b, $\Pi$ is the interface area, and $f(\sigma_i^b)$ is the local interface stress function, which is defined based on the multi-axial Hoffman failure criterion (Hoffman, 1967). This function is used to determine where local debonding might occur along the bone-implant interface (Pal et al., 2009). The probability of local interface failure $f(\sigma)$ is given by:

$$f(\sigma) = \frac{1}{S_t S_c} \sigma_n^2 + \left(\frac{1}{S_t} - \frac{1}{S_c}\right)\sigma_n + \frac{1}{S_s^2}\tau^2 \qquad (9)$$

where $S_t$ and $S_c$ are the uniaxial tensile and compressive strengths, respectively, $S_s$ is the shear strength, and $\sigma_n$ and $\tau$ are normal and shear stresses at the bone-implant interface, respectively. For $f(\sigma) \gg 1$, a high probability of failure is expected, whereas for $f(\sigma) \ll 1$ the risk of interface failure is low. Tensile, compression, and shear strengths of the bone can be expressed as a function of bone density according to the power law relation obtained by Pal et al. (2009):

$$S_t = 14.5\rho^{1.71}, S_c = 32.4\rho^{1.85}, S_s = 21.6\rho^{1.65} \qquad (10)$$

The bone density distribution can be obtained through a CT-scan data of bone and then used in Eq. (10) to find the effective mechanical properties of the bone, from which the local interface failure is determined via Eq. (9). Finally, the interface failure index, F(b), is evaluated by means of Eq. (8).

The expressions of bone resorption after implantation, and mechanical failure of bone-implant interface described in this section are used in the finite element analysis to evaluate the objective functions to be optimized.

Figure 4:
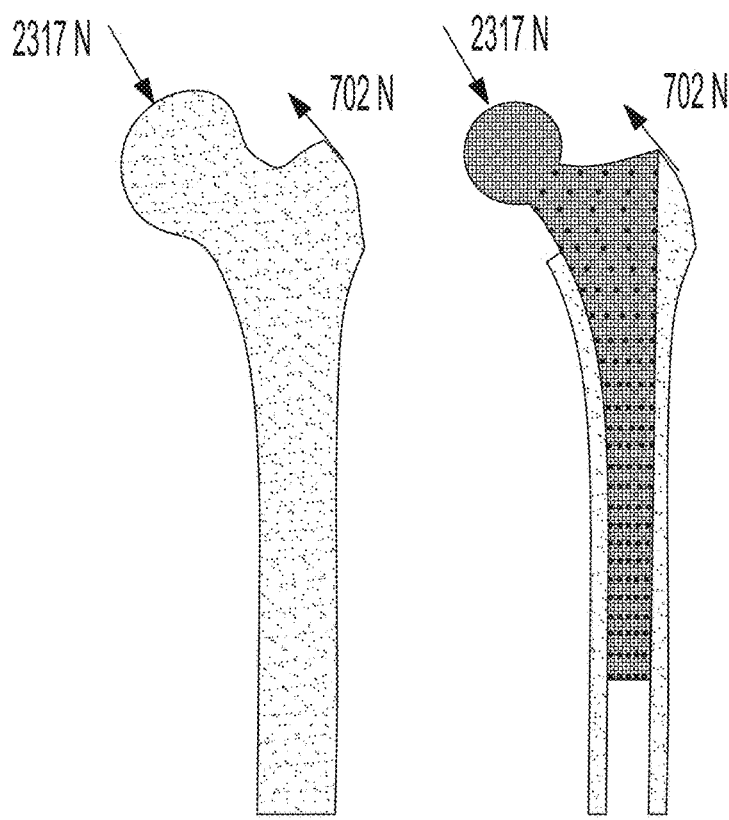
FIG. 4 illustrates a 2D Finite element models of the femur (left) and the prosthesis implanted into the femur (right).

The left hand side of FIG. 4 shows the geometry of the left femur considered in this work along with the appropriate loads and boundary conditions. The grid depicts the domain of the implant to be designed with a lattice material of graded properties. These data have been obtained from the work of Kuiper and Huiskes (1992). The 3D geometry of the femur is simplified into a 2D model where the thickness of the stem and bone varies such that the second moment of area about the out-of-plane axis does not vary in both models (Hedia et al., 2006). Furthermore, the implant material is designed to be an open cell lattice to ease bone ingrowth in the implanted stem and obtain a full bond. Although bone ingrowth does not exist in a postoperative situation, it can appear later if local mechanical stability is guaranteed. The minimization of interface stress reduces the possibility of occurrence of interface micromotion and instability. Therefore, to decrease the computational cost required by a stability analysis based on a non-linear frictional contact model, the prosthesis and the surrounding bone are assumed fully bonded.

The load case represent daily static loading during stance phase of walking (Carter et al., 1989). The distal end of the femur is fixed to avoid rigid body motion. For the material properties of the model, 20 GPa was considered as the Young's modulus of the cortical bone and 1.5 GPa for the proximal bone. The Poisson's ratio is set to be 0.3.

Figure 5:
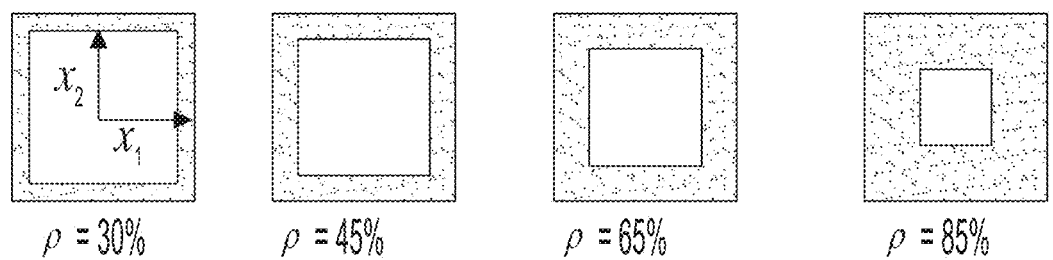
FIG. 5 illustrates a 2D hollow square unit cell for given values of relative density.

FIG. 5 shows the unit cell geometry used for the tessellation of the whole implant. The gradients of material properties are governed by the lattice relative density, which as model variable is controlled by the cell size and wall thickness of the hollow square. For the material property of the implant, Ti6Al4V, which is a biocompatible material commonly used in EBM, was considered. Its mechanical properties are the following: 900 MPa for the yield strength of the solid material, 120 GPa for Young's modulus, and 0.3 for Poisson's ratio.

The procedure or method 20 disclosed herein for the design of a graded cellular implant requires both multiscale analysis and multiobjective optimization, as shown in FIG. 2. The variables of the lattice model are the relative densities attributed to 130 sampling points, 26 rows along the prosthetic length and 5 columns along the radial direction, as shown in the right side of FIG. 4. The number of sampling points has been chosen to be 130 to limit the computational time required for the analysis and optimization, while providing a reasonable resolution for the relative density distribution. For a more refined density distribution, the number of sample points can be increased. Their values have been constrained in the range $0.1 \leq \rho < 1$ to prevent elastic buckling from occurring in the unit cell prior to yielding. The values of the relative density between the sampling points are obtained through linear interpolation. Although not considered in the current research, the shape of the implant could be included in the vector b as a design variable (FIG. 2).

Figure 6:
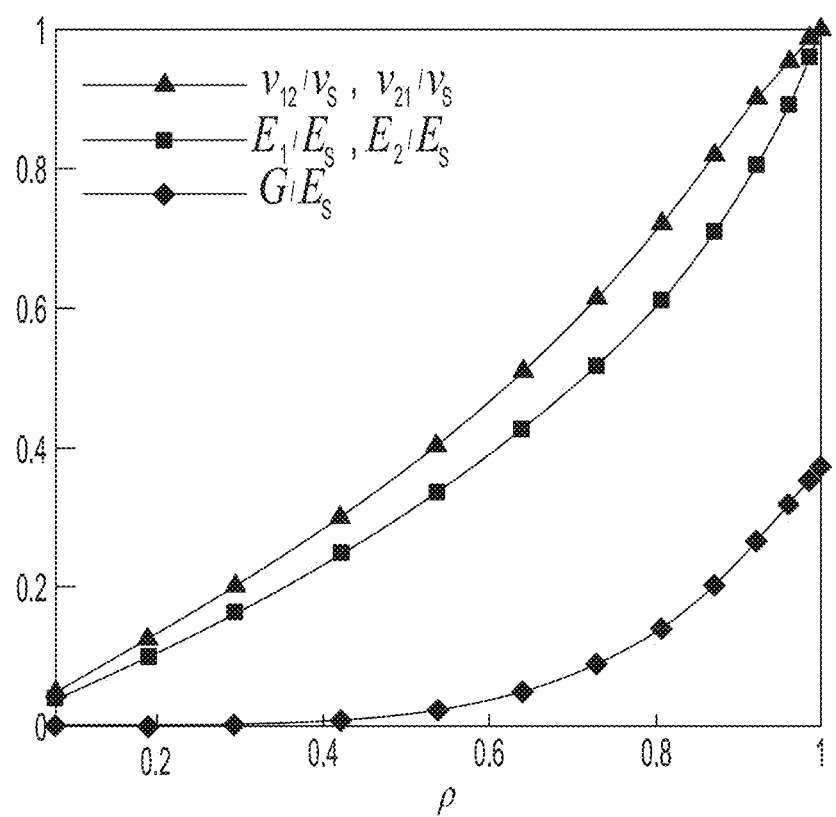
FIG. 6 illustrates a curve showing the effective Young's modulus of 2D square lattice versus relative density, where solution points obtained through homogenization theory are fitted with the least squares method.

Initial values of relative density are assigned to each element of the FE model, created in ANSYS (Canonsburg, Pa., U.S.A). The stiffness matrix of each element is calculated through a computational code, 2DHOMOG, which obtains the homogenized stiffness matrix of the square unit cell as a function of relative density. FIG. 6 shows the results which are first obtained at discrete points of relative density. To obtain the continuous functions for the properties, it was calculated through the least squares method the expressions (Table 1) for two ranges of relative density, i.e. $\rho<0.3$ and $\rho>0.3$.

TABLE 1

Effective mechanical properties of the square unit cell as a function of relative density

| | $\rho < 0.3$ | $0.3 < \rho < 1$ |
|---|---|---|
| $\dfrac{E_1}{E_s} = \dfrac{E_2}{E_s}$ | $0.58(\rho)^{1.0\text{-}15}$ | $1.27(\rho)^2 - 0.52(\rho) + 0.23$ |
| $\dfrac{G}{E_x}$ | $0.093(\rho)^{3.07}$ | $1.26(\rho)^3 - 1.33(\rho)^2 + 0.51(\rho) - 0.065$ |
| $\dfrac{v_{21}}{v_x} = \dfrac{v_{12}}{v_s}$ | $0.7(\rho)^{1.05}$ | $0.68(\rho)^2 + 0.28(\rho) + 0.06$ |

The functions allow the values of the stiffness for a given relative density assigned to each sample point to be found for the finite element model of the implant. It is noted that the expressions of Young' moduli and Poisson's ratios in the $x_1$ and $x_2$ directions do not change since the cell thickness is uniform.

Once the stress and strain regimes of the cellular material have been calculated, the non-dominated sorting genetic (NSGA-II) algorithm (Deb et al., 2002) is employed to solve the multiobjective optimization problem. The strain energy within the bone and the stress distribution at the bone-implant interface is then calculated and used in Eqs. (7-8) to evaluate the objective functions. The initial population is then sorted based on the non-domination front criterion. A population of solutions, called parents, are selected from the current population, based on their rank and crowding distance. Then, generic operators are applied to the population of parents to create a population of off-springs. Finally, the next population is produced by taking the best solutions from the combined population of parents and off-springs. The optimization continues until the user-defined number of function evaluations reaches 25000 (Deb et al., 2002).

For each point in the objective function space, the stress recovery procedure is applied to verify whether the stresses are admissible. To apply this procedure, the average macroscopic strain inside each unit cell is found. To this end, the position of each unit cell within the implant is obtained after imposing a proper cell tessellation, which in this work has been set to be uniform. The size of the unit cell is selected as small as possible to capture the relative distribution contour with higher resolution. For a relative density of 0.1, the square cell sizes for the cell wall thickness of either 70 or 100 µm have been selected respectively as 1.36 and 1.8 mm. Once the position of the unit cells have been obtained, 3×3 Gauss points are assigned to each cell. The values of relative density and macroscopic strain at these points are obtained from the relative density distribution and macroscopic strain field. For Gauss points located outside the implant border, the values are linearly extrapolated from those located at the neighboring points inside the implant domain. Using a Gaussian quadrature integration (Zienkiewicz and Taylor, 2005) the average relative density and macroscopic strain of each cell are calculated. The local stress distribution and the yield safety factor of each cell are obtained through the von Mises stress criterion. The procedure is applied to all unit cells of the selected optimal design located on the Pareto frontier and the minimum local safety factor of a cell is specified as design safety factor.

Figure 7:
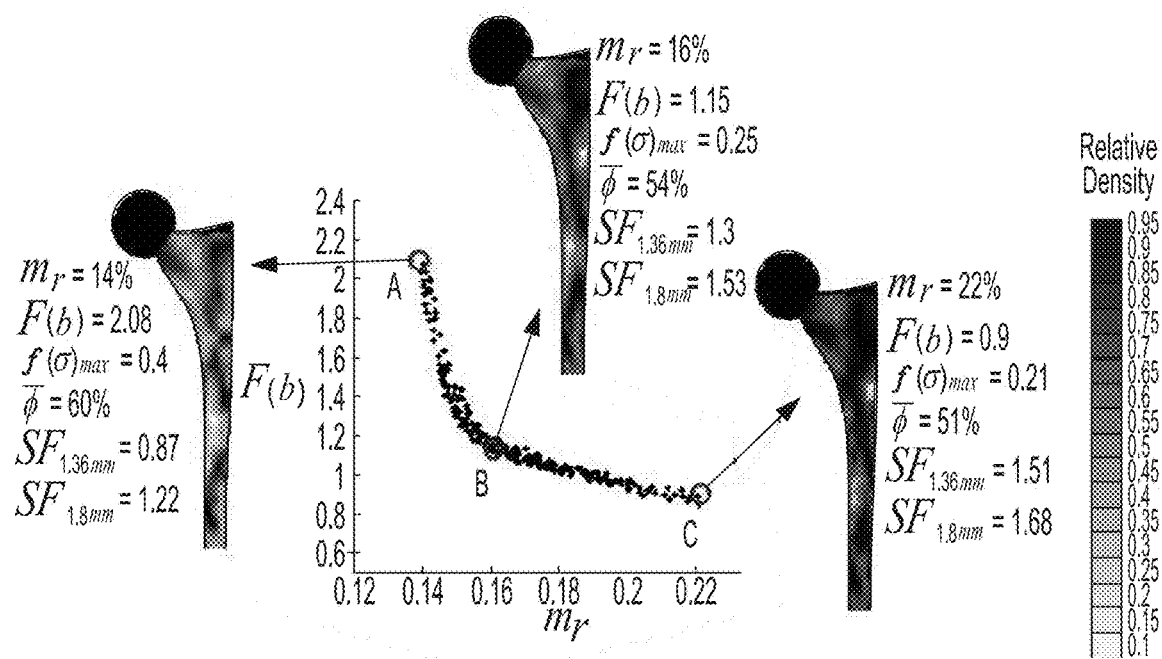
FIG. 7 illustrates the trade-off distributions of relative density for the optimized cellular implant in accordance with an embodiment.

The advantage of multiobjective optimization with a posteriori articulation of preference is that a set of optimum solutions are available without requiring the designer to choose in advance any weighting factors to the objective function. Once the whole set of Pareto solutions has been determined, the designer has the freedom to select the desired solution based on the importance of bone mass preservation relative to the amount of interface stress. FIG. 7 shows all the optimum solutions, i.e. the relative density distribution, for a hip stem implant with graded cellular material. The x axis represents the amount of bone resorption for the implanted hip; on the y axis is the interface failure index. Among the optimal solutions, three representative relative density distributions were examined: the extreme points, A and C, of the Pareto frontier, for which one objective function has importance factor 0 and the other 100%, and a solution B characterized by a 50% weight factor. For each solution, in FIG. 7 are given the following performance metrics: bone resorption ($m_r$), interface failure index (F(b)), maximum interface failure ($f(\sigma)_{max}$), average porosity of each stem ($\bar{\phi}$), and design safety factor (SF) after implementing the stress recovery procedure. The maximum interface failure $f(\sigma)_{max}$ is included since F(b), which quantifies only the overall effect of the implant stiffness on the interface stresses, is not sufficient to provide information on the probability of failure.

As seen from the performance metrics in FIG. 7, the porosity of solutions A, B, and C, is greater than 40%, which is satisfactory for bone ingrowth (Bragdon et al., 2004). By comparing implants C and A, an increase is seen of the implant porosity from point C to A results in an implant stiffness decrease, which on one hand lowers bone loss and on the other hand enhances the risk of interface failure. When solution B is compared to C, a reduction of 8% of bone resorption is noted with a slight increase of the peak value of the interface failure. On the other hand, by contrasting solution B to A, a significant increase (60%) of the peak value of interface failure is seen, which is still below the Hoffman failure strength, while a minor reduction (2%) of the amount of bone resorption is demonstrated. The main benefit of solution A is the maximum porosity of the microstructure that can promote bone ingrowth. While B might be the preferred solution with respect to low bone resorption and interface failure, other parameters should be taken into account for the selection of the best implant. These include patient's bone characteristics, the range of activity, age, and desired level of bone mass preservation after implantation.

For prescribed geometric loading and constraint conditions, the metrics of resorbed bone mass ($m_r$) and distribution of interface stress ($f(\sigma^b)$) of the optimal solution B were compared with those of i) a currently-used fully dense titanium stem and ii) a cellular implant with a uniformly distributed relative density of 50%. FIGS. 8 and 9 illustrate the results of the comparison.

For the solid titanium stem, the amount of bone resorption calculated through Eq. (7) is 67%, and the interface failure index F(b) obtained from Eq (8) is 1.33. Using the distribution of $f(\sigma)$ generated around the titanium stem (FIG. 9a), it was observed that the maximum value of interface failure (0.51) occurs at the distal end of the implant. As expected, this implant is much stiffer than the surrounding bone, thereby resulting in a higher amount of bone resorption. For the numerical validation, the interface shear stress of the titanium implant at the proximal region is also compared with the one obtained by Kowalczyk for a 3D model (Kowalczyk, 2001). The mean and the maximum values of interface shear stress for the 3D titanium implant in the work by Kowalczyk (2001) are 0.57 and 2.8 MPa, respectively. These values are 0.31 and 2.15 MPa respectively for the titanium implant in this paper. The contribution to the higher level of shear stress in the 3D model of Kowalczyk is the distribution of shear force on a smaller area. In Kowalczyk's study (2001), the implant and bone are bonded only at the proximal region, while in our work the whole bone-implant interface is bonded, which results in a decrease of the mean and the maximum values of interface shear stress.

The cellular implant with uniform relative density of 50% is approximately three times more flexible than the titanium stem. This implant can qualitatively simulate the behavior of an implant made out of tantalum foam. For this stem, the amount of bone resorption and the interface failure index are about 34% and 2.87, respectively, and the interface failure is maximum (0.71) at the edge of proximal region. Compared to the solid titanium implant, the amount of bone resorption decreases by 50%, whereas the maximum interface failure increases about 40%. This shows that a decrease of the implant stiffness with uniform porosity distribution aiming at reducing bone resorption has the undesirable effect of increasing the risk of interface failure at the proximal region. This result confirms the findings of the previous work by Kuiper and Huiskes (1992).

Figure 8A:
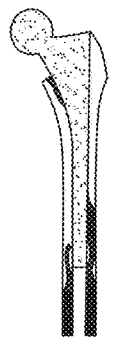
FIG. 8 illustrates the distribution of bone resorption around (a) fully dense titanium implant, (b) cellular implant with uniform relative density of 50%, (c) graded cellular implant, and (d) an enlarged view of the unit cell having different microscopic stress field.
Figure 8B:
Figure 8C:
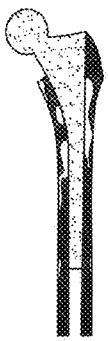
Figure 8D:
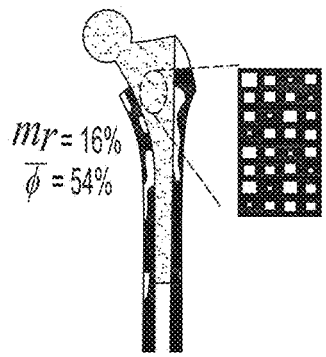
Figures 9A, 9B, 9C:
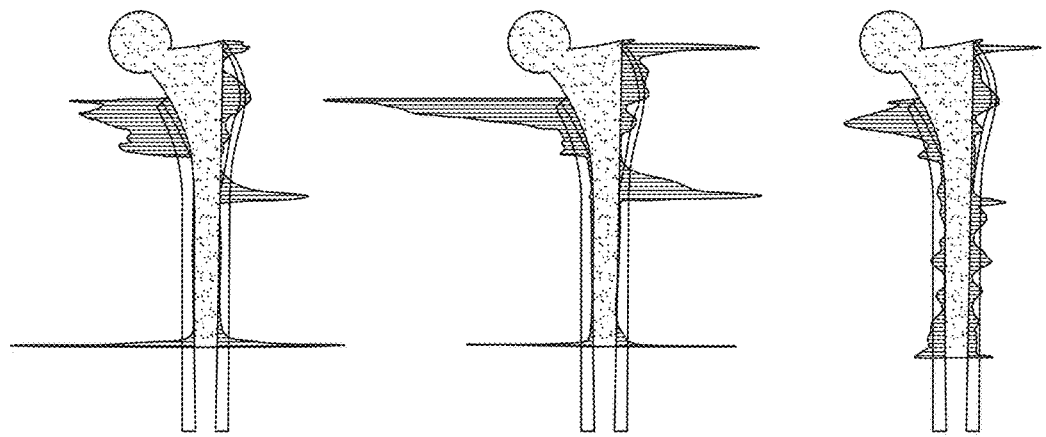
FIG. 9 illustrates the distribution of local interface failure around (a) fully dense titanium implant, (b) cellular implant with uniform relative density of 50%, (c) graded cellular implant.

FIGS. 8c and 9c show the results for the graded cellular implant B. Its bone resorption and interface failure index are 16% and 1.15 respectively. The peak value of the local interface failure is 0.25. Compared to the titanium stem, both the amount of bone resorption and the interface failure peak decrease by 76% and 50%, respectively. With respect to the uniformly-distributed cellular implant, the decrease of bone resorption and interface failure peak is of 53% and 65%, respectively. A graded cellular implant with optimized relative density distribution is thus capable of reducing concurrently both the conflicting objective functions. In particular, bone resorption reduces as a result of the cellular material which makes the implant more compliant; the interface stress, on the other hand, is minimized by the optimized gradients of cellular material.

Figure 10:
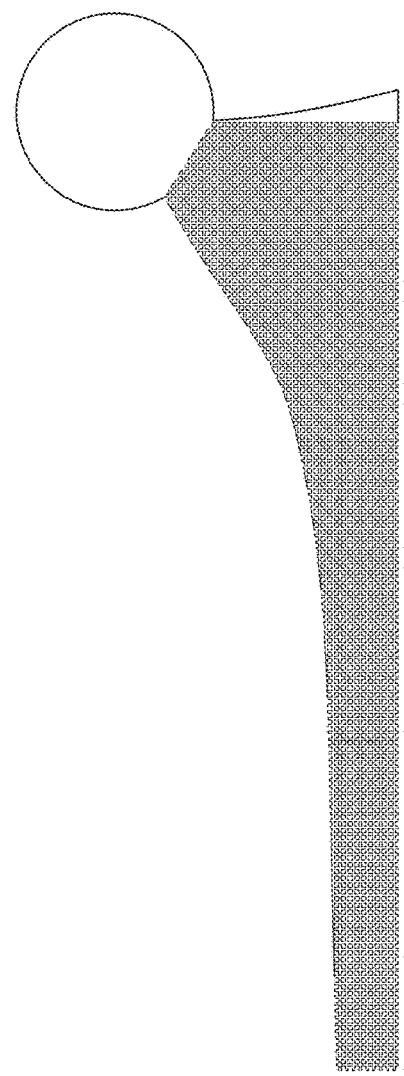
FIG. 10 illustrates a polypropylene model of the optimal graded cellular implant in accordance with an embodiment.

FIG. 10 shows the polypropylene prototype of solution B, which was manufactured with the 3D printer Objet Connex500™. A uniform tessellation and a square unit cell of 1.8 mm size were assumed to draw the model. The cell geometry was calculated from the average relative density obtained from the method described in this paper. An STL file of the graded cellular implant, solution B, was finally used for rapid prototyping.

Following is the fatigue analysis and design of the lattice material of the implant constructed in accordance with the present invention and illustrating a series of optimum relative density distribution of the implant that meet the fatigue requirements.

With reference now to FIGS. 11 to 25, the microstructure fatigue failure methodology is described. An orthopaedic hip implant is expected to support dynamic forces generated by human activities. To avoid progressive and localized damage caused by daily cyclic loading, the prosthesis is to be designed for fatigue under high cycle regime. Recently, a methodology has been developed to design a novel hip implant made of a cellular material with a periodic microarchitecture (Khanoki and Pasini, 2012). In contrast to current hip replacement implants typically made out of a fully solid material which can be coated with a spongy layer, this implant is completely porous with a lattice microstructure displaying graded property distribution. The advantage of controlling the microarchitecture is twofold. First, the overall implant can be designed to be more compliant, which reduces stress shielding and bone resorption (Behrens et al., 2008; Glassman et al., 2006; Huiskes et al., 1992; Pettersen et al., 2009). Second, the material porosity can be optimized to also reduce bone-implant interface stresses, thereby lowering implant micromotion. Although encouraging, these results have been obtained by applying a static loading regime to the implant, thus neglecting the impact of an applied cyclic loading that generally boosts the risk of fatigue failure.

In literature, there are several experimental and numerical studies focusing on the fatigue analysis of hip implants (Baleani et al., 1999; Hedia et al., 1996; Kayabasi and Ekici, 2007; Li et al., 2002; Nganbe et al., 2011; Ploeg et al., 2009; Raimondi and Pietrabissa, 1999; Senalp et al., 2007). For example, fatigue loading conditions, ISO 7206/3, have been applied to a hip stem to predict its elastic stress via large deflection finite element analysis (Ploeg et al., 2009). It has been demonstrated via experiments that the high cycle fatigue-life of hip stems can be adequately predicted by using alternative fatigue theories, such as Morrow, Smith-Watson-Topper (SWT), and Goodman. The Soderberg theory has also been used to design a cemented implant for infinite life; the results have been proved to be accurate although more conservative than those obtained with Goodman and Gerber theories (Hedia et al., 1996; Kayabasi and Ekici, 2007).

Among the biocompatible materials used for reconstructive orthopaedics, porous tantalum has been recently proved to be effective in facilitating bone ingrowth. For this reason, porous tantalum has been lately the object of studies aiming at characterizing its fatigue fracture mechanisms (Sevilla et al., 2007; Zardiackas et al., 2001). Similar to open cellular foams, porous tantalum has a random cellular microstructure which is typically imparted by the manufacturing process, which involves a chemical deposition of pure tantalum on carbon skeleton (Bobyn et al., 2004; Murr et al., 2010; Murr et al., 2009). Due to its pore structure, the fracture propagation of porous tantalum under fatigue has been observed similar to that of open-cell foams (Sevilla et al., 2007; Zardiackas et al., 2001; Zhou and Soboyejo, 2004). It has been observed that the bending dominated failure mode of the unit cell (Gibson, 2005; Liu and Du, 2011; Vigliotti and Pasini, 2012) at the cell joints nucleates cracks that propagate throughout a strut until the final break (Li et al., 2012; Sevilla et al., 2007; Zardiackas et al., 2001). The joints are indeed the weakest parts of a cellular material, because stress peaks localize in those regions and thus severely reduce fatigue strength. However, if the geometry of the cell joints, i.e. the locations where the struts converge, is designed to level out any curvature discontinuity (Abad et al., 2012), then the joint strength can be significantly increased, thereby improving the fatigue strength of the cellular material.

While several analytical methods have been proposed to study the fatigue life of cellular structures (Cote et al., 2006; Côté et al., 2007a; Côté et al., 2007b; Huang and Liu, 2001a, b; Huang and Lin, 1996; Olurin et al., 2001), the majority fail to accurately capture the real stress distribution generated in the lattice cells (Simone and Gibson, 1998). To overcome this problem, more recently a fatigue design methodology has been introduced to model the elastic-plastic behavior of cellular materials, and used to generate fatigue design diagrams for cellular materials (Abad et al., 2012) under uni-axial and shear loading for relative density $\rho \leq 0.3$ This method is first extended in this paper to model multiaxial loadings of cellular materials under infinite fatigue life. The approach is then applied to the fatigue design of a graded cellular hip implant loaded under cycling forces of walking. Two representative cell topologies are selected to design the hip implant: the square lattice, which is a bending dominated behaviour, and the Kagome cell, whose main deformation is caused by the strut stretching. The results obtained in this paper are numerically validated through the multilevel method for damage analysis (Ghosh et al., 2001; Raghavan and Ghosh, 2004). The performance of the two lattice implants is compared in terms of bone resorption, interface stress, and mechanical strength. Finally, a 3D proof-of-concept of a graded cellular implant with a cubic cell is fabricated to assess the manufacturability of the lattice microarchitecture.

2 FATIGUE ANALYSIS OF CELLULAR MATERIALS

The deformation and failure mechanisms of a structure with heterogeneous material can occur at both macro and microscopic length scales. Experimental studies have shown that a cellular material under repetitive loading develop cracks at the microscale in regions with high stress concentration, from which fracture propagates throughout the strut cross sections (Sevilla et al., 2007; Zardiackas et al., 2001; Zhou and Soboyejo, 2004). Since the micromechanisms of deformation and fracture play a crucial role in the fatigue resistance of a cellular material, it is essential in the design of a cellular component to capture and account for the microscopic stress and strain distribution. Here, we resort to Asymptotic Homogenization (AH) theory to determine the homogenized properties of the cellular material via the analysis of a representative volume element (RVE). AH method has been widely used in multiscale analysis of composite materials (Kalamkarov et al., 2009; Kanouté et al., 2009), topology optimization (Bendsøe and Kikuchi, 1988; Bendsøe and Sigmund, 2003; Díaaz and Kikuchi, 1992; Guedes and Kikuchi, 1990; Hassani and Hinton, 1998; Suzuki and Kikuchi, 1991), and hierarchical design of materials and structures (Coelho et al., 2008; Coelho et al., 2011; Gonçalves Coelho et al., 2011; Rodrigues et al., 2002). For a given macroscopic strain and stress distribution, AH can capture with a high accuracy the microscopic stress and strain regime.

Recently, AH has been also used to propose a computational procedure for the fatigue design of lattice materials (Abad et al., 2012). Yield and ultimate strength of lattice materials have been determined for relative density $\rho \leq 0.3$, and used to construct modified Goodman diagrams of selected lattices under uni-axial and shear loading. This method is here extended to construct the Soderberg fatigue diagram for fatigue failure analysis of cellular structures under multiaxial loading conditions for the whole range of relative density.

To obtain the stress distribution within the unit cell through AH, the following local problem defined on the RVE should be solved (Guedes and Kikuchi, 1990; Hollister and Kikuchi, 1992):

$$\int_{Y_C} E_{ijpm}\varepsilon_{ij}^1(v)\varepsilon_{pm}^{*kl}(u)dY = \int_{Y_C} E_{ijkl}\varepsilon_{ij}^1(v)\bar{\varepsilon}_{kl}dY \qquad (1)$$

where $\varepsilon_{ij}^1(v)$ is the virtual strain, $\varepsilon_{ij}^{*kl}(u)$ is the microstructural strain corresponding to the component kl of the macroscopic strain tensor $(\bar{\varepsilon}_{kl})$, $Y_c$ is the solid part of the cell, and $E_{ijkl}$ is the local elasticity tensor. The main underlying assumption of AH, the periodicity of field quantities at the microscale, is ensured by imposing periodic boundary conditions on the RVE edges; hence the nodal displacements on the opposite edges are set to be equal (Hassani, 1996; Hollister and Kikuchi, 1992). Considering the assumption of small deformation and elastic material behavior, the solution of equation (1) leads to a linear relation between the macroscopic $(\bar{\varepsilon}_{ij})$ and microscopic $(\varepsilon_{ij})$ strain through the local structural tensor $M_{ijkl}$:

$$\varepsilon_{ij} = M_{ijkl}\bar{\varepsilon}_{kl}, \; M_{ijkl} = \frac{1}{2}(\delta_{ik}\delta_{jl} + \delta_{il}\delta_{jk}) - \varepsilon_{ij}^{*kl} \qquad (2a, b)$$

where $\delta_{ij}$ is the Kronecker delta. For a two-dimensional case, three independent unit strains are required to construct the $M_{ijkl}$ matrix. The effective stiffness tensor $E_{ijkl}^H$ is then calculated by the following equation:

$$E_{ijkl}^H = \frac{1}{|Y|}\int_{Y_C} E_{ijpm}M_{pmkl}dY \qquad (3)$$

where |Y| is the volume of the entire unit cell with voids. The homogenized stiffness matrix relates the macroscopic strains to the macroscopic stresses of the homogenized material. Once the local structure tensor, $M_{ijkl}$, is obtained, the microscopic stresses corresponding to the macroscopic strain can be obtained via the following equation:

$$\sigma_{ij} = E_{ijkl}M_{klmn}\bar{\varepsilon}_{mn} \qquad (4)$$

Using the homogenized stiffness matrix, the microscopic stress distribution $\sigma_{ij}$ can, therefore, be related to the multiaxial macroscopic stress $\bar{\sigma}_{ij}$ by the following relation:

$$\sigma_{ij} = E_{ijkl}M_{klmn}(E_{rsmn}^H)^{-1}\bar{\sigma}_{rs} \qquad (5)$$

The von Mises stress distribution over the microstructure is then used to capture the yield surface of the unit cell expressed as follow:

$$\bar{\sigma}_{ij}^y = \frac{\sigma_{ys}}{\max\{\sigma_{vM}(\bar{\sigma}_{ij})\}}\bar{\sigma}_{ij} \qquad (6)$$

where $\bar{\sigma}_{ij}^y$ is the yield surface of the unit cell, $\sigma_{ys}$ is the yield strength of the bulk material, and $\sigma_{vM}(\bullet)$ is the von Mises stress of the microstructure corresponding to the applied macroscopic stress. The fatigue surface of the unit cell can be obtained through the product of the unit cell yield strength with the ratio of the endurance limit and yield strength of the bulk material as:

$$\bar{\sigma}_{ij}^e = \bar{\sigma}_{ij}^y \frac{\sigma_{es}}{\sigma_{ys}} \qquad (7)$$

where $\bar{\sigma}_{ij}^e$ is the endurance limit of the unit cell and $\sigma_{es}$ is the endurance limit of the bulk material. These properties are required to construct the Soderberg fatigue diagram under multiaxial loading condition:

$$\frac{\bar{\sigma}_{ij}^m}{\bar{\sigma}_{ij}^y} + \frac{\bar{\sigma}_{ij}^a}{\bar{\sigma}_{ij}^e} = \frac{1}{SF} \quad (8)$$

where the mean and alternating macroscopic stresses, respectively, $\bar{\sigma}_{ij}^m$ and $\bar{\sigma}_{ij}^a$ are calculated by the following relations:

$$\bar{\sigma}_{ij}^m = \frac{\bar{\sigma}_{ij}^{max} + \bar{\sigma}_{ij}^{min}}{2}, \bar{\sigma}_{ij}^a = \frac{\bar{\sigma}_{ij}^{max} - \bar{\sigma}_{ij}^{min}}{2} \quad (9a, b)$$

$\bar{\sigma}_{ij}^{max}$ and $\bar{\sigma}_{ij}^{min}$ are the multiaxial macroscopic stresses that cause, respectively, the highest and the lowest values of the von Mises stress in the microstructure.

In this study, the above procedure is applied to design a 2D graded cellular implant. To generate the lattice, we select the square and Kagome unit cells, as representative of bending and stretching dominated topologies, and we characterize their mechanical and fatigue properties.

2.1 Unit Cell Characterization for Multiscale Mechanics and Fatigue Analysis

Figure 13B:
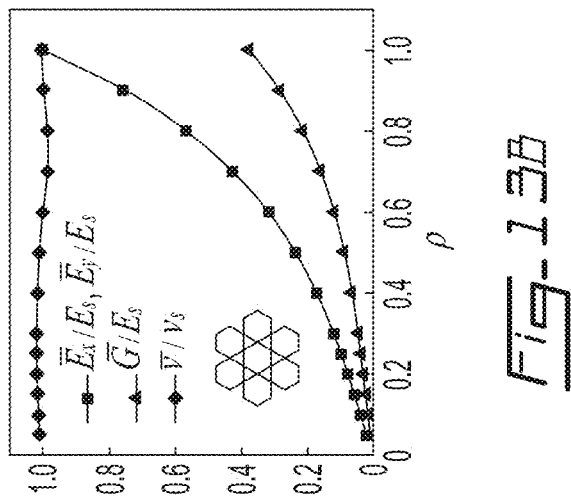
FIGS. 13(a) and (b) are graphs of the effective elastic constants as a function of relative density for the (a) square and (b) Kagome lattices.
Figure 13A:
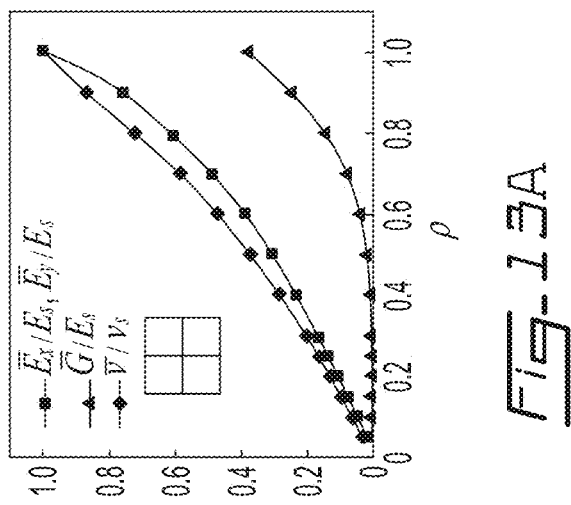

The effective elastic moduli and yield surfaces of square and Kagome lattices, with uniform wall thickness, are obtained by using AH for the range of relative density $0.05 \leq \rho \leq 1$. FIG. 13 illustrates the homogenized elastic constants of the cell topologies as a function of relative density. As can be seen, the effective Young's modulus, shear modulus, and Poisson's ratios converge to the elastic constants of the base solid material as the relative density reaches one. Since the Kagome cell topology is elastically isotropic and the square has orthotropic symmetry, the Young's modulus is equal in both x and y directions. The square cell has a superior elastic stiffness due to the capacity of realigning the cell walls along the loading direction, but it exhibits very low stiffness under shear loading as a result of cell wall bending.

Figure 15:
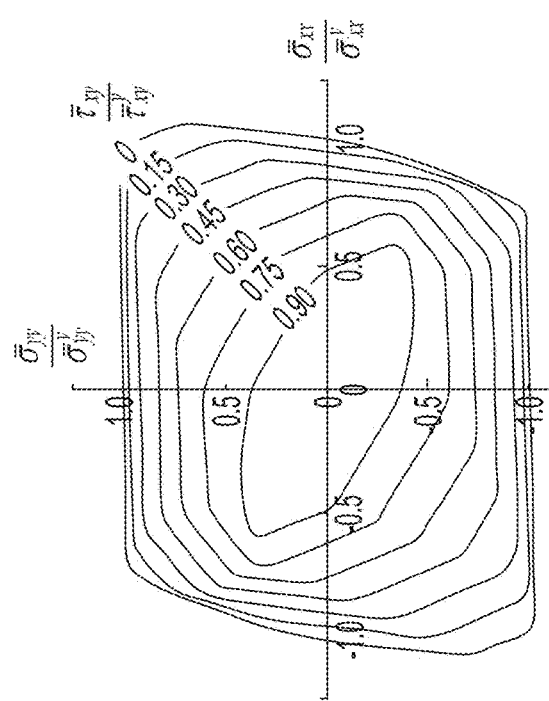
FIGS. 15(a) to (d) illustrate the yield surface of a Kagome cell topology under combined multiaxial macroscoic stress state ($\bar{\sigma}_{xx}$, $\bar{\sigma}_{yy}$, and $\bar{\tau}_{xy}$) for a relative density ρ=30%.
Figure 15:
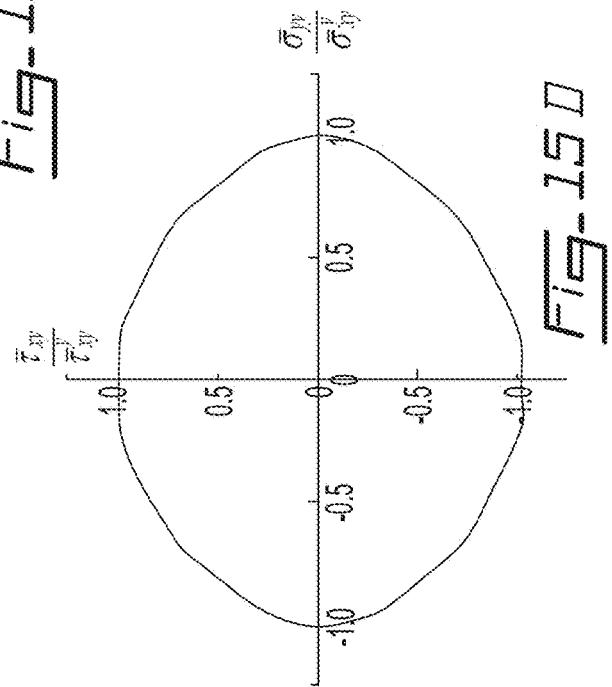
Figure 15:
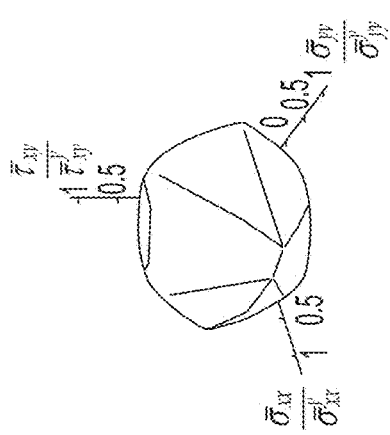
Figure 15:
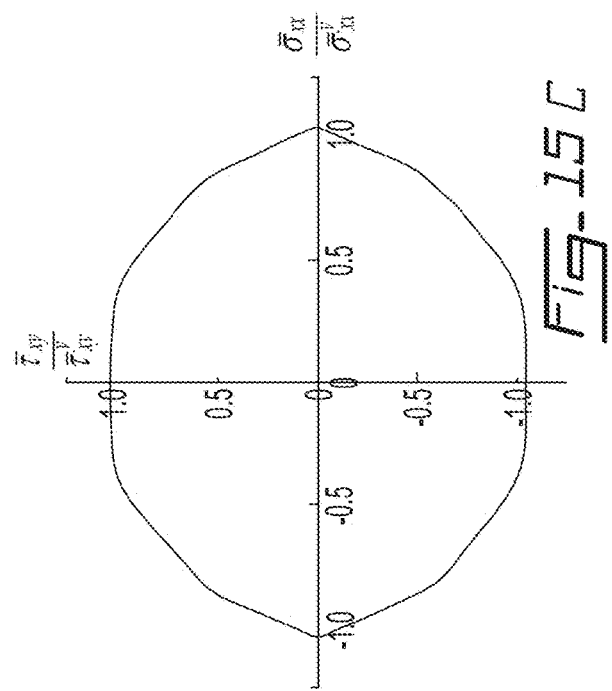

The yield surfaces of the cell topologies are also obtained for multiaxial macroscopic stresses. As shown in equation (6) and being in linear elasticity, the location of the yield point on the yield surface of each lattice is obtained by multiplying the macroscopic stress with the ratio of the material yield strength and the maximum von Mises stress. FIGS. 14 and 15 show the yield surfaces normalized with respect to the yield strength of the square and Kagome lattices in the uniaxial and shear loading directions at a given relative density. FIG. 14 refers to the square lattice for the relative density of 50%, and FIG. 15 pertains to the Kagome cell for the relative density of 30%. We selected 30% for the Kagome, because for a 50% relative density the base material almost completely fills the triangular voids, and thus the Kagome structure cannot be realized.

Once the yield surface is determined, the multiaxial endurance limit of the cell can be obtained by scaling the yield surface with the coefficient given in equation (7). These data can be inserted into equation (8) for the infinite-life design of cellular structures under multiaxial fatigue loading conditions. For design purposes, it is often convenient to resort to closed-form expressions that can approximately describe the geometry of a yield surface. For this reason, the Table (FIG. 11) lists the functions along with relative fitting parameters of the yield surfaces for the unit cells here under investigation. For the square cell (FIG. 14(b), a pyramid with an elliptical base is used to resemble the yield surface. $F_{xy}^*$ (FIG. 11) governs both the slenderness ratio and the inclination of the major axis of the elliptical base. For the Kagome cell (FIG. 15(b)), the yield surface is approximated by a parallelogram, and m, and $m_2$ (FIG. 11) are the slopes of the parallelogram lines, expressed as a function of the relative density. The parameters $\bar{\sigma}_{xx}^y$, $\bar{\sigma}_{yy}^y$, $\bar{\tau}_{xy}^y$ (FIG. 11) are the yield strength of the unit cell under uni-axial and shear stresses. FIGS. 16(a) and 16(b) show the variation of the yield strength as a function of relative density. When the material is fully dense, the yield strength is equal to that of its solid material. A common feature in the plots of FIG. 16 is the abrupt decrease of the effective yield strength for decreasing values of relative density. The reason for this is the presence of stress concentration at the cell joints, which locally increases the level of stress. We note here that the fatigue strength of the lattice can be significantly improved by optimizing the cell shape and removing the curvature discontinuity at the joints (Abad et al., 2012).

3 FATIGUE DESIGN OF A HIP IMPLANT WITH CONTROLLED LATTICE MICROARCHITECTURE

Figure 17:
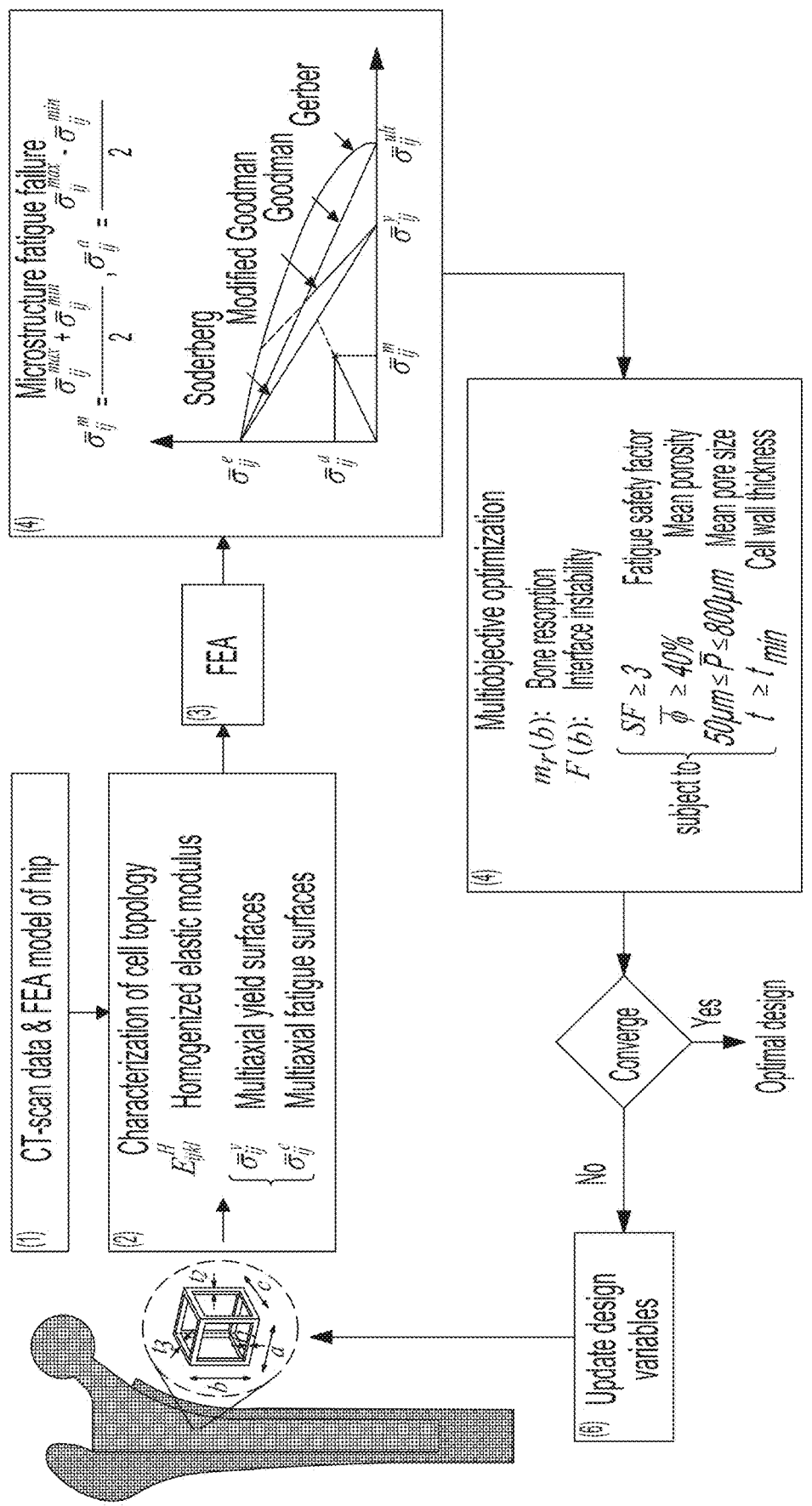
FIG. 17 is a flow chart illustrating the fatigue design methodology of a graded cellular hip implant.

FIG. 17 illustrates the methodological steps to design a graded cellular implant for infinite fatigue life. The approach combines multiscale mechanics and multiobjective optimization. The former deals with the scale-dependent material structure, where the local problem of the RVE is first solved, and then the effective elastic moduli and yield strength are obtained and used as homogenized properties of the macroscopic model of the implant. The latter handles the conflicting nature of bone resorption and implant interface stress. A fatigue failure theory can thus be embedded in the procedure to design the implant for infinite fatigue life. A brief description of the main steps identified by the numbers in the flowchart is given in FIG. 17.

(1) A finite element model of the bone is created by processing CT-scan data of a patient bone.

(2) A 3D lattice microstructure is considered as the building block of the implant, and it is characterized through AH. The homogenized elastic modulus, yield and fatigue surfaces of the cell topology under multiaxial loading conditions are obtained.

(3,4) From FEA, the mean and alternative macroscopic stresses are obtained, and used in the fatigue design diagram to determine the design safety factor (SF). In this study, the Soderberg's fatigue failure criterion is considered for the analysis.

(5) The two conflicting objective functions, bone resorption $m_r(b)$ and interface failure index F(b), are minimized via a multiobjective optimization strategy subjected to a set of inequality constraints. The amount of bone resorption is determined by comparing the local strain energy per unit of bone mass between the pre-operative and the postoperative situation, as described in detail in (Khanoki and Pasini, 2012). The interface failure index F(b) is expressed by the following relation:

$$F(b) = \max\left\{\frac{f(\sigma)_i}{\frac{1}{A}\int_A f(\sigma)_i dA}\right\} \quad (10)$$

where i is the loading case (1, 2, and 3), and A is the interface area. $f(\sigma)$ is defined as the interface failure caused by shear stress, and is expressed as $$\frac{\tau}{S_s},$$

where $\tau$ is the local shear stress at the bone-implant interface, and $S_s$ is the bone shear strength. In equation (10), the interface failure $f(\sigma)$ is normalized with its average over the bone-implant interface area. The minimization of F(b) will lead to a design with minimum and uniform shear stress distribution at the interface. The shear strengths of bone can be expressed as a function of bone apparent density according to the power law relation obtained by Pal et al. (Pal et al., 2009):

$$S_s = 21.6 \rho^{1.65} \tag{11}$$

During the optimization procedure, the values of mean porosity and pore size are selected to ensure bone ingrowth (Bragdon et al., 2004; Harrysson et al., 2008), and the minimum thickness of the cell walls is determined by the resolution of the manufacturing process, i.e. the manufacturing limits.

(6) The vector b of the design variables is updated until the set of non-dominated solutions of the Pareto front are obtained.

The methodology described above is now applied for the design of a 2D graded cellular implant. Square and Kagome cell topologies, which are characterized in the previous section, are considered as the cell architecture of the implant. The lattice is designed to support the cyclic load of walking and is optimized to reduce bone resorption and interface stress. The FEA model of the femur and implant, loading and boundary conditions, and the results are described in the following sections.

4 DESIGN OF A 2D FEMORAL IMPLANT WITH A GRADED CELLULAR MATERIAL

4.1 2D FEM Model of the Femur

Figures 18A, 18B:
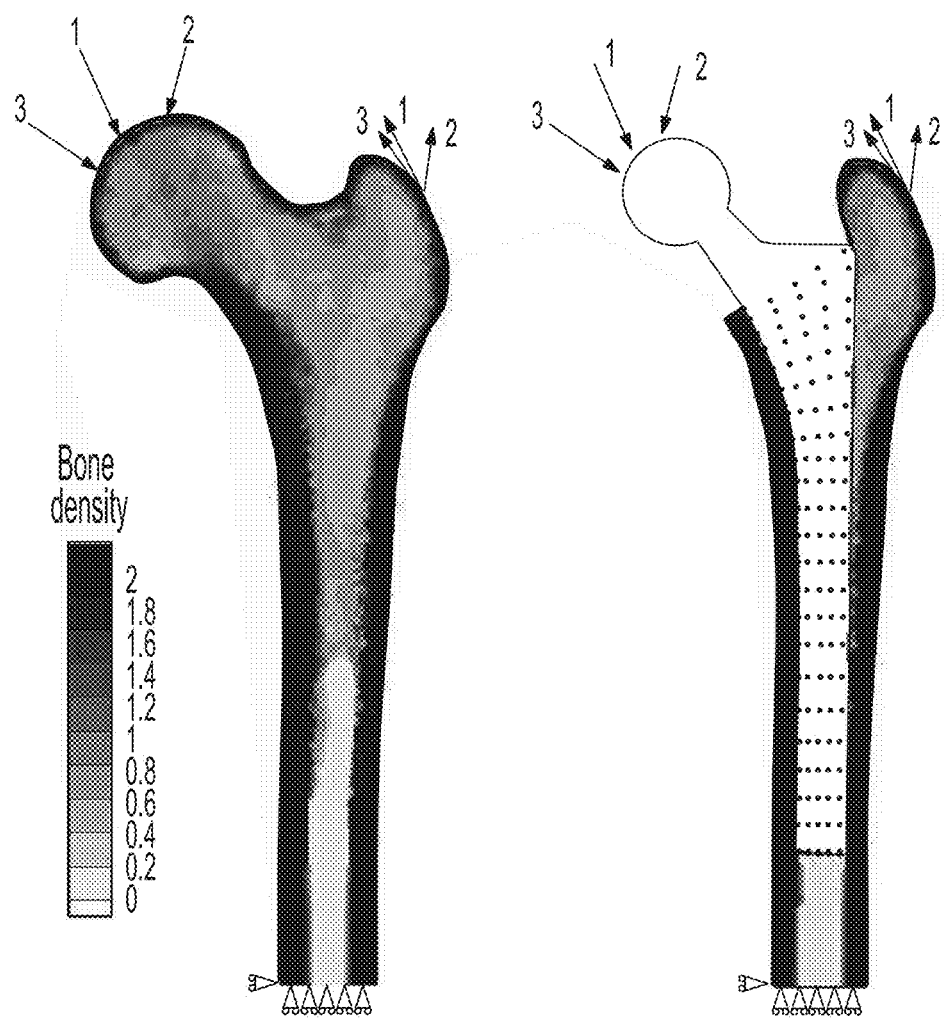
FIGS. 18(a) and (b) are side and section views of (a) 2D Finite element models of the femur and (b) the prosthesis implanted into the femur.

FIG. 18(a) shows the geometry of the femur considered in this work along with the applied loads and boundary conditions. CT scan data of a 38-year-old male, obtained through the visible human project (VHP) database of the national library of medicine (NLM, USA), is used to construct the 3D model of the femur. The mid-frontal section of the femur is considered for the 2D model geometry. To account for the three dimensional structural integrity of the femur, a side plate is also considered for the 2D model. The 2D model and the side plate have variable thickness such that the second moment of area about the out-of-plane axis of the 2D model does not differ from that of the 3D model (Huiskes et al., 1987; Weinans et al., 1992). The apparent density $\rho$ for each element of the FE model is then determined by the Hounsfield value (HU) measured from CT data. A linear relation between HU and apparent density is considered, where the maximum value of HU corresponds to the most dense region of the cortical bone, where the maximum value of apparent density is 2.0 g/cm³, and HU value of water and its apparent density are equal to zero. From the apparent density distribution, the effective elastic moduli of bone are obtained through the relation (Austman et al., 2008; Baca et al., 2008; Peng et al., 2006):

$$\begin{cases} E = 1904\rho^{1.64} & \rho < 0.95 \\ E = 2065\rho^{3.09} & 0.95 < \rho \end{cases} \tag{12}$$

$$v = 0.3$$

An isotropic material model is considered for the bone, as this simplification does not lead to a noticeable difference from those results obtained by assigning orthotropic material property to the bone (Baca et al., 2008; Peng et al., 2006). The distal end of the femur is fixed to avoid rigid body motion, and three loading cases, 1, 2, and 3, representing the cyclic load during walking movements are applied to the hip joint and the abductor (Carter et al., 1989; Pérez et al., 2010; Weinans et al., 1992). The magnitudes and the direction of the hip joint (the abductor) forces are, respectively, for the different load cases: 1) 2317 N at 24° from vertical (702 N at 28° from vertical), 2) 1158 N at 15° from vertical (351 N at 8° from vertical), 3) 1548 N at 56° from vertical (468 N at 35° from vertical). ANSYS (Canonsburg, Pa., U.S.A) is used to build, mesh, and solve the 2D model. Assuming in-plane loading conditions, a 2D eight-node element type (Plane 82) is used since it can model curved boundaries with high accuracy.

4.2 FEM Model of the Cellular Implant

FIG. 18(b) illustrates the model of a cementless prosthesis implanted into the femur. The grid depicts the domain of the implant to be designed with a functionally graded lattice material. The variable of the lattice model is the relative density attributed to 115 sampling points, 23 rows along the prosthetic length and 5 columns along the radial direction. The values of relative density are constrained in the range $0.1 \leq \rho \leq 1$ to prevent elastic buckling in the unit cell from occurring prior to yielding (Wang and McDowell, 2004). The relative density distribution throughout the implant is obtained by linear interpolation between the corresponding values at the sampling points. The homogenized stiffness matrix and the yield surfaces of each element are then computed from those values respectively illustrated in FIG. 11. The former is employed to assemble the global stiffness matrix for the Finite Element (FE) solver, and the latter is used to construct the Soderberg diagram for fatigue analysis.

Since the implant is designed to have a cellular microstructure with suitable pore size for bone ingrowth, it is assumed that the prosthesis and the surrounding bone are fully bonded (Khanoki and Pasini, 2012; Kowalczyk, 2001). This choice significantly decreases the computational cost required for the stability analysis based on a non-linear frictional contact model (Viceconti et al., 2000). Although bone ingrowth does not exist in a postoperative situation, it can appear later, if local mechanical stability is guaranteed. It is expected, however, that the minimization of interface stress reduces the risk of interface micromotion and instability (Kowalczyk, 2001).

For the material property of the implant, we consider Ti6Al4V (Parthasarathy et al., 2010), which is a biocompatible material commonly used in Electron Beam Melting (EBM), with mechanical properties: 900 MPa for the yield strength of the solid material, 600 MPa for the fatigue strength at $10^7$ cycles, 120 GPa for the Young's modulus, and 0.3 for the Poisson's ratio.

5 RESULTS

The procedure illustrated in section 3 is applied for the fatigue design of the implant after having calculated the yield and fatigue strengths of the microstructure, as described in section 2. To solve the multiobjective optimization problem, the non-dominated sorting genetic (NSGA-II) algorithm (Deb et al., 2002) is here used. Once the initial population is evaluated, a set of solutions, called parents, are selected based on their rank and crowding distance. Genetic operators are then applied to the population of parents to create a population of off-springs. Finally, the next population is produced by taking the best solutions from the combined population of parents and off-springs. The optimization continues until the user-defined number of function evaluations reaches 25000 (Deb et al., 2002). The computational cost required to run the optimization process in a single 2.4 GHz Intel processor was about 300,000 CPU seconds, 3 and a half days. Parallel computing with a PC cluster will considerably reduce the computational time, since each function evaluation can be performed independently.

Figure 19A:
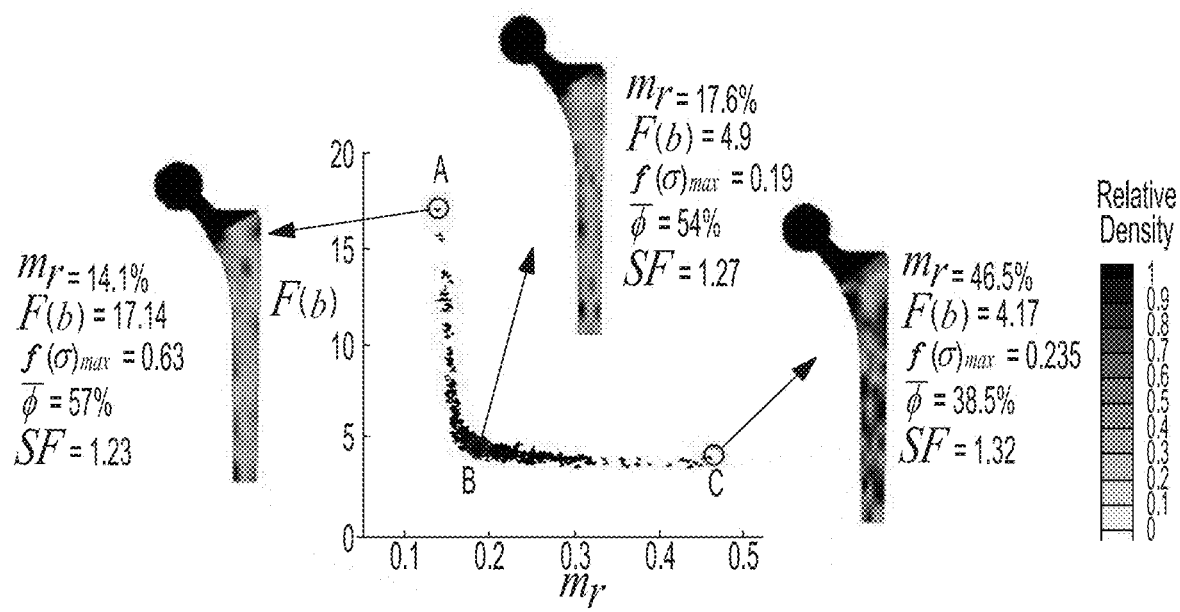
FIGS. 19(a) and (b) are illustrations of trade-off distributions of relative density for the optimized cellular implant made of (a) square and (b) Kagome lattices.
Figure 19B:
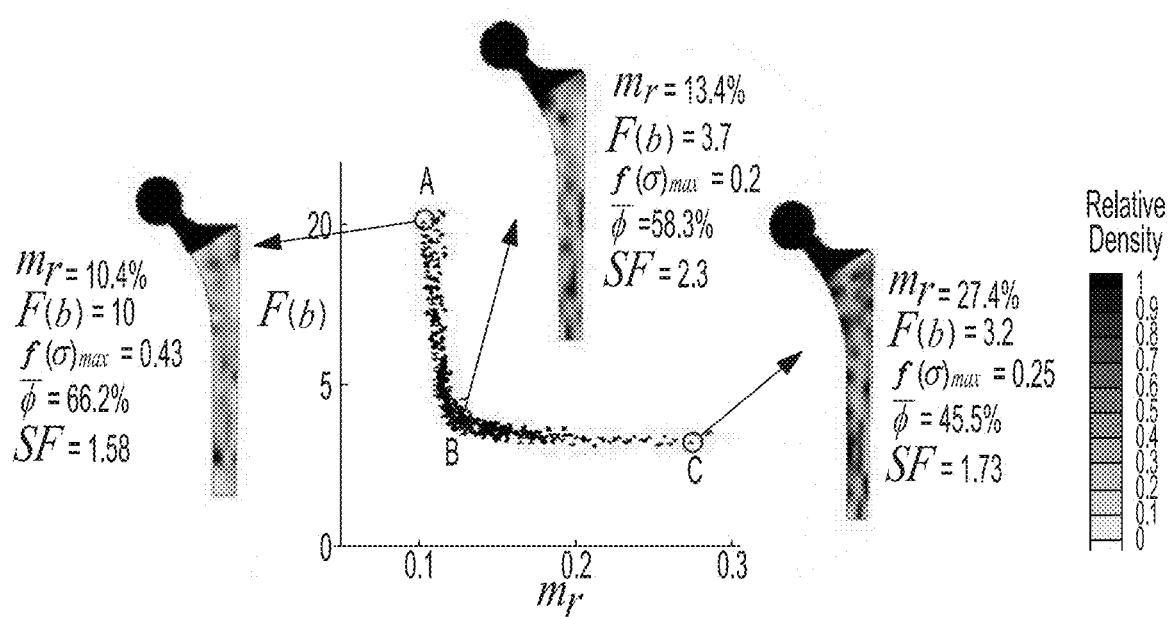

The advantage of formulating and solving the problem as a multiobjective optimization task is that a set of optimum solutions are available without requiring the designer to choose in advance any weighting factors for the objective function. Once the whole set of Pareto solutions has been determined, the surgeon has the freedom to select the desired implant design based on the relative importance of the objective functions. FIGS. 19(*a*) and 19(*b*) show all the optimum relative density distributions for a hip stem implant designed with square and Kagome cell topologies. The x axis represents the amount of bone resorption for the implanted hip, and on the y axis is the interface failure index. Among the optimal solutions, we examine three representative relative density distributions: the extreme points, A and C, of the Pareto frontier, for which one objective function has importance factor 0 and the other 100%, and a solution B characterized by a 50% weight factor. For three solutions, A, B, and C, the following characteristics are also illustrated in FIG. 19: the amount of bone resorption ($m_r$), interface failure index (F(b)), maximum shear interface failure ($f(\sigma)_{max}$), average porosity of each hip stem ($\bar{\phi}$), and design fatigue safety factor (SF) from the Soderberg diagram.

Through comparison of the results, we observe that an increase in implant porosity from point C to A results in a stiffness decrease of the implant, which, on one hand, lowers bone loss, while, on the other, enhances the risk of interface failure. As can also be seen compared to the implant with square lattice, the implants designed with Kagome cells have better performance in terms of bone loss and interface shear stress. If solutions B in FIGS. 19(*a*) and (*b*) are compared, we note that the amount of bone loss decreases of about 4.2% and the shear stress concentration factor at the interface reduces by up to about 24.5%. While both implants have been designed for infinite fatigue life, the fatigue safety factor has improved approximately 81% for the implant designed by the graded Kagome cell topology. The reason for this is that Kagome is a stretching dominated cell with higher mechanical strength compared to the square cell for a given relative density. This provides a wider range of relative density for the optimization search to choose the design variable from, and control the stress distribution at the interface. Moreover, lower values of relative density can be selected to increase the implant flexibility and reduce bone resorption. We remark here that beside mechanical strength, other physical parameters, such as pore shape, interconnectivity, permeability and diffusivity of the unit cell, should be taken into account for the selection of a proper lattice cell for bone tissue scaffolding (Hollister, 2005; Hollister et al., 2008; Kang et al., 2010; Reilly and Engler, 2010; Van Bael et al., 2012). Further research is required in the near future to address these aspects.

6 NUMERICAL RESULT VALIDATION

During the optimization procedure, AH is applied for the multiscale analysis of the cellular implants. Although this method is quite effective in computing the stress and strain distribution at each scale, its accuracy needs to be investigated especially at regions where the underlying assumption, Y-periodicity of field quantities, is not satisfied. This can include regions with a high gradient of field quantities or in the vicinity of borders (Dumontet, 1986; Ghosh et al., 2001; Lefik and Schrefler, 1996; Raghavan and Ghosh, 2004; Takano et al., 2003; Yuan and Pagano, 2003). The multilevel computational method can be used for the analysis of these critical regions (Ghosh et al., 2001; Raghavan and Ghosh, 2004). This method decomposes the computational domain into two levels of hierarchy: a) the detailed cellular microstructure and b) the homogenized medium. The region of interest, composed of a cellular microstructure, is modeled by a fully detailed FE analysis; to assess the validity of the periodicity assumption the FE results are compared with those obtained from the homogenization method. The following criterion can be defined to measure the departure from the periodicity conditions:

$$\frac{F(\sigma_{ij}, \varepsilon_{ij})^{FEA} - F(\sigma_{ij}, \varepsilon_{ij})^{RVE}}{F(\sigma_{ij}, \varepsilon_{ij})^{RVE}} \geq C \qquad (13)$$

where the function F is a function of ($\sigma_{ij}$, $\varepsilon_{ij}$) and can be defined, for example, as the average of the microscopic stress over the RVE. The superscript FEA refers to the evaluation of the function F via a detailed finite element analysis of a given microstructure. The macroscopic displacement solution, obtained from the homogenized model, is imposed on the unit cell boundary of the detailed FE model, and the stress and strain distribution within the microstructure is obtained. The superscript RVE, on the other hand, corresponds to the computation of F for each RVE through the imposition to the unit cell of a macroscopic strain with periodic boundary conditions. C is a user defined adaptation tolerance; C=0.1 can be considered as an appropriate transition value to map the homogenized model to the detailed analysis of the local microstructure (Raghavan and Ghosh, 2004). Here as functions, a) the average and b) the maximum value of von Mises stress over the unit cell, are considered respectively to evaluate the validity of the periodicity condition at macroscale, and to assess the accuracy of AH in capturing the yield strength of the microstructure.

Figure 20A:
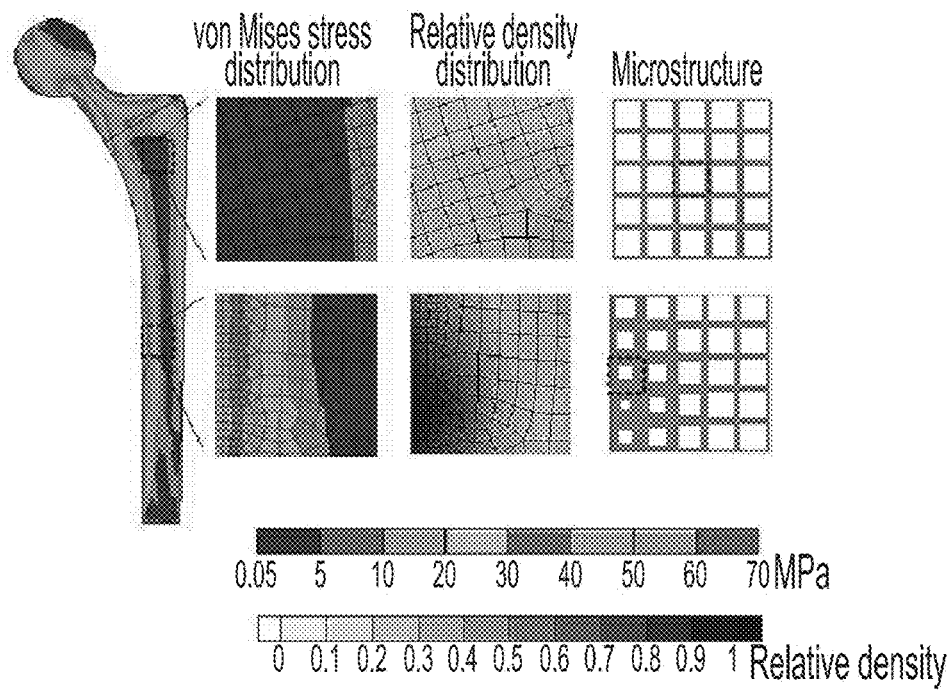
FIGS. 20(a) and (b) are magnified views of regions used to assess the accuracy and validity the AH model (left and middle) with respect to a detailed FE analysis of a 5×5 lattice microstructure (right).
Figure 20B:
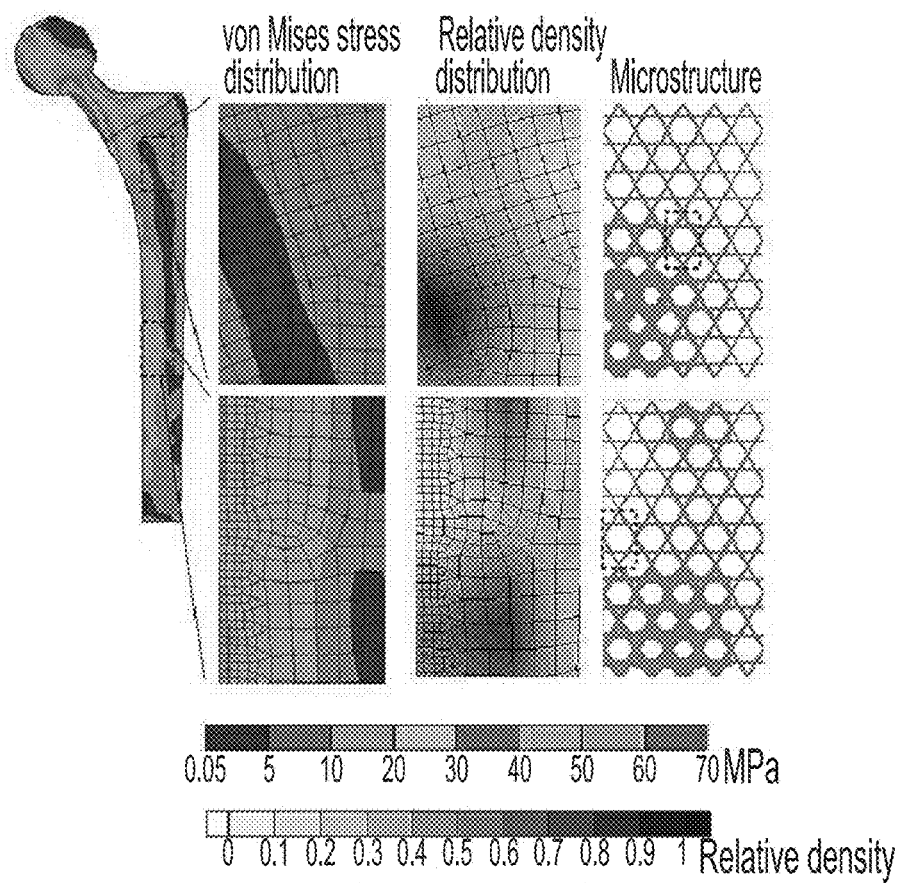
Figure 21A:
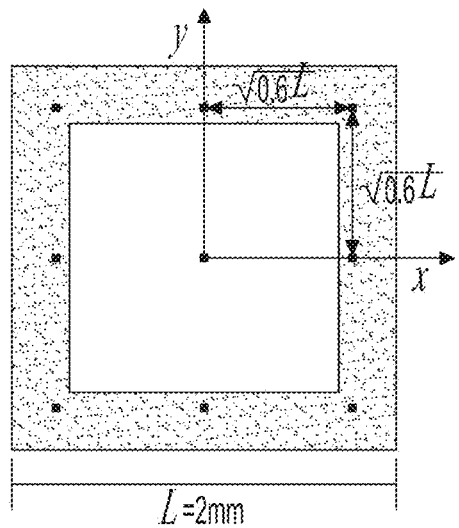
FIGS. 21(a) and (b) are illustrations of (a) 3×3 Gauss points in the RVE; (b) superposition of the RVE on the macroscopic mesh of the homogenized model.
Figure 21B:
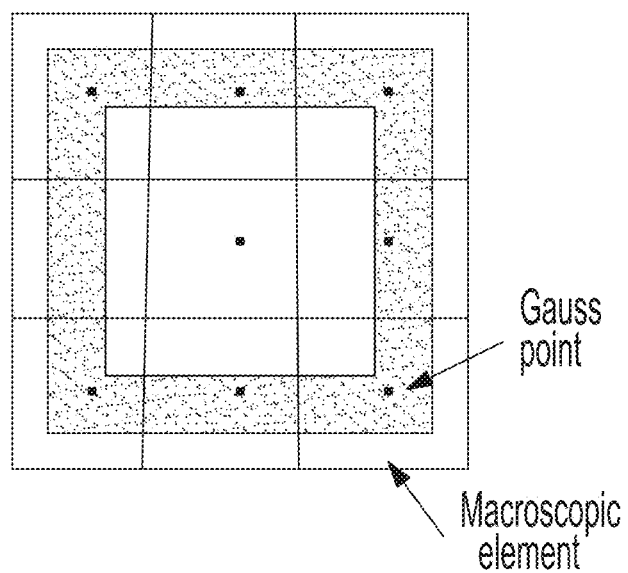

We investigate two regions to assess the accuracy of AH: one at the proximal part, where the Y-periodic assumption of field quantities is expected, and the other at the vicinity of the implant boundary, where this assumption does not hold. FIG. 20 illustrates the macroscopic von Mises stress distribution throughout the square and Kagome lattice implants associated with the loading condition number 1 applied to the hip joint. The mesh of the macroscopic elements at the vicinity of the implant border has been refined to capture the interface stresses with a higher resolution. The stress and relative density distribution, shown in FIG. 20, corresponds to the solutions B in FIG. 19. We can observe almost a uniform stress distribution in the proximal region of the implants; however, there is higher stress gradient at the vicinity of the implant boundary especially for the square lattice implant, which might affect the periodicity assumption of AH. To perform the detailed FEA and assess the accuracy of AH results, the microstructures need to be constructed at the specified regions. For the square cell, a 2×2 mm size is selected to satisfy the manufacturing constraint ($t_{min} \geq 0.1$ mm for $\rho \geq 0.1$) and to uniformly tessellate the regions with a 5×5 cells block. For the Kagome topology, the RVE has a rectangular shape with the same cell size as the square in the x direction. To produce the cell geometry from the relative density distribution, 3×3 Gauss points are assigned to each cell, as shown in FIG. 21. Using a Gaussian quadrature integration (Zienkiewicz and Taylor, 2005), the average relative density of the RVE is obtained as:

$$\bar{\rho} = \sum_{i=1}^{9} \sum_{j=1}^{9} W_{ij} \rho_{ij} \quad (14)$$

where $\rho_{ij}$ and $W_{ij}$ are the relative density and weight factors at each Gauss point, respectively. The relative density at each Gauss point is obtained with respect to its local coordinates within the macroscopic element of the homogenized model (FIG. 21). Once the average relative density is obtained, the cell geometry can be constructed for both the square and Kagome lattices, as depicted in FIG. 20. The displacement of the macroscopic solution is then imposed on the boundary of the cells block (Raghavan and Ghosh, 2004), so as to calculate the stress distribution of the microstructure. The average and the maximum von Mises stress for the unit cells is then computed and used in equation (13) to assess the validity and accuracy of the AH results.

To recover the stress distribution throughout the microstructure via AH, the average macroscopic strain is needed over the RVE. FIG. 22 illustrates the macroscopic strains distribution, $\bar{\varepsilon}_{xx}$, $\bar{\varepsilon}_{yy}$, $\bar{\tau}_{xy}$, over the regions proximal and closed to the boundary of the square and Kagome lattice implants. As can be seen, there is a uniform variation of macroscopic strains in the proximal region, while there is high strain gradient close to the boundary which might affect the AH periodicity assumption. Therefore, the validity and the accuracy of the results obtained by the homogenization method needs to be verified. Using the procedure described above, the average macroscopic strain for each unit cell is computed; the strain tensor is used in equation (2) to obtain the microscopic strain distribution throughout the microstructure, from which the microscopic stresses are calculated via the constitutive equation of the base material. For the block at the proximal region, the microscopic stress distribution of the unit cell located at the center of the block is compared with those obtained from a detailed FEA. For the block at the implant border, the stress distribution within the cell in the middle of the first column of FIG. 8 is considered. Based on the results of several analyses, we have observed that a change of the block position has a negligible effect on the unit cell stress distribution if the location of the selected unit cell is prescribed within the implant.

The von Mises stress distribution of the unit cells, obtained by AH and by detailed FE analysis, are given in the Table (FIG. 12). The average and the maximum value of von Mises stress over the unit cells obtained by AH are also compared with the detailed FE analysis, and the relative errors, defined by equation (13), are illustrated in FIG. 12. As can be seen, the stress distribution at the microscopic level can be captured with a reasonable accuracy, particularly for those cells located in the middle of the block.

For the square unit cell, the average and the maximum value of von Mises stress can be estimated with an error of 0.98% and 7.1%, respectively. For the unit cells close to the boundary, a higher relative error for the microscopic stresses is anticipated as the Y-periodic assumption is not satisfied. As can be seen in FIG. 12, the relative error for the average and the maximum von Mises stress for the Kagome lattice located at the implant boundary is 3.8% and 18.6%, respectively. Considering C=0.1 as the criterion for creating the transition from the homogenized model to the fully detail analysis, it can be seen that the periodicity assumption can capture the average of the macroscopic stress distribution throughout the implant with accuracy.

Here, we consider the maximum relative error of 18.6% as an acceptable value for the assessment of material yielding at the microscopic level, specifically if we deem that a fully detailed FEA of the implant might be almost unfeasible. The computational cost required to perform a single simulation of a fully detailed FE model of a cellular implant on a 2.4 GHz Intel processor is about 1,500 CPU seconds. Considering 25000 function evaluations for the optimization procedure, the simulation time required for the fully detailed FE model would be $3.75 \times 10^7$ seconds which is about 100 times higher than the simulation time needed for the analysis of a homogenized model.

7 DISCUSSION

In this section, we examine the results within the context of a performance comparison of other implants currently available in the market as well as on the manufacturability aspects. As a benchmark for the comparative study, a fully dense titanium implant is chosen. Its bone resorption and the distribution of local shear interface failure are determined, and then compared with those of the cellular implants represented by solutions B in FIG. 19 for both the square and Kagome lattice.

As expected, FIG. 23(*a*) shows that for a fully dense implant, bone mass loss is about 71.4%. This initial postoperative configuration of bone loss is in good agreement with that in literature (Huiskes et al., 1992; Weinans et al., 1992). A high amount of bone resorption is found throughout the medial and lateral part of the femur around the fully dense stem. Compared to the fully dense implant, the amount of initial postoperative bone loss of the square and Kagome lattice implants decreases, respectively, by 53.8% and 58%. This shows that the design of a flexible implant through a graded cellular material has the beneficial effect of improving the load-sharing capacity of the implant with the surrounding bone, thereby reducing bone resorption.

FIG. 24 shows the distribution of the local shear interface failure, $f(\sigma)$, around the fully dense titanium, square and Kagome lattice implants. At each point, the maximum value of interface failure caused by any of three loading cases is shown. Since the function $f(\sigma)$ is the interface shear stress normalized with respect to the local shear strength of the bone, high probability of interface failure is expected for $f(\sigma) \geq 1$, whereas for $f(\sigma) < 1$ the risk of interface failure is low. For the fully dense titanium implant, we observe that the maximum value of shear interface failure occurs at the distal end with magnitude of 0.96. This means that the shear stress is almost equal to the shear strength of the host bone, which may cause interface micromotion and prevent bone ingrowth. For the square and Kagome lattice implants, the maximum shear interface failure reduces significantly of about 79% to 0.19 and 0.2, respectively. An optimized graded distribution of the cellular microarchitecture can reduce the stress distribution at the implant interface. For the numerical validation, the interface shear stress of fully dense titanium implant is also compared with those obtained in literature (Kuiper and Huiskes, 1992; 1996). We have that the interface shear stress varies from 3.8 MPa at the proximal region to the maximum value of 42 MPa at the distal end, which is in good agreement with the stress regime available in (Kuiper and Huiskes, 1992; 1996).

The fatigue analysis of the fully dense titanium implant shows that its safety factor is 4.95. Although this value is about two times higher than the corresponding value of the Kagome lattice implant, a safety factor of 2.3 for Kagome lattice implant can be still considered as a reasonably safe margin for the design against fatigue fracture. To improve the implant fatigue strength, either a lattice with smooth cell geometry could be considered (Abad et al., 2012), or the implant core can be designed as fully dense.

To assess the manufacturability of the lattice microstructure of the implant, we fabricate via rapid prototyping (Objet Connex500 (Objet-Geometries, 2011)) a polypropylene prototype of solution B (square lattice). FIG. 25 shows the proof-of-concept implant with a uniform tessellation of unit cells with 2 mm size. Using the projection of the cell geometry in a 2D plane, the average relative density of each cell was computed from the method described above. The cubic cells with a uniform wall thickness were then used as a building block to construct the implant. Finally, an STL file of the graded cellular implant was used for rapid prototyping. The supporting material deposited during the manufacturing process was washed out with a water jet, and a graded cellular implant with interconnected porosity respecting bone ingrowth requirements was fabricated. No sign of fracture or incomplete cell walls was observed, showing the structural integrity of the cellular implant.

8 CONCLUSIONS

A hip-joint implant with a graded lattice material can improve the load sharing capacity of the implant with the surrounding bone tissues as well as decrease the amount of bone resorption. The implant microstructure has been designed against fatigue fracture to support cyclic loads in the hip joint. Asymptotic homogenization has been used for the multiscale analysis of the structure to obtain the stress distribution at the macro and micro scale, while the Soderberg fatigue criterion has been integrated in the procedure to design the implant for infinite fatigue life. The numerical results obtained have been validated via a detailed FE analysis.

Square and Kagome lattices have been used in a multi-objective optimization procedure to simultaneously minimize bone resorption and interface failure. It has been found that for the square and Kagome lattice implants the amount of bone loss is respectively 54% and 58% lower than that of a fully dense titanium implant. The maximum shear interface failure at the distal end of the implants decreases as well of about 79%. The implant designed with a Kagome lattice is 81% more fatigue resistant than that with a square lattice, but it has 53% lower safety factor compared to the fully dense titanium implant. The fatigue resistance of the cellular implant can be improved by modifying the micro and macro geometric parameters, such as selecting a cell topology with improved fatigue life or reinforcing the implant core. While the invention has been described with particular reference to the illustrated embodiment, it will be understood that numerous modifications thereto will appear to those skilled in the art. Accordingly, the above description and accompanying drawings should be taken as illustrative of the invention and not in a limiting sense.

The above description is meant to be exemplary only, and one skilled in the art will recognize that changes may be made to the embodiments described without departing from the scope of the disclosure. For example, while generally described with respect to hip implants, it is to be understood that the present method and system can also be used to produce other implants such as a knee, elbow, wrist, ankle, shoulder and/or dental implants. Still other modifications which fall within the scope of the present disclosure will be apparent to those skilled in the art, in light of a review of the disclosure, and such modifications are intended to fall within the appended claims.

REFERENCES

The below listed documents are incorporated by reference herein in their entirety.

Abad, E. M. K., Khanoki, S. A., Pasini, D., 2013, "Fatigue Design of Lattice Materials via Computational Mechanics: Application to Lattices with Smooth Transitions in Cell Geometry", International Journal of Fatigue, vol 47, pp. 126-136, 2013.

Khalil Abad, E. M., Pasini, D., Cecere, R., 2012, "Shape Optimization of Stress Concentration Free Lattice for Self-Expandable Nitinol Stent-Grafts", Journal of Biomechanics, 45, 1028-1035.

Abdul-Kadir, M. R., Hansen, U., Klabunde, R., Lucas, D., Amis, A., 2008, "Finite Element Modelling of Primary Hip Stem Stability: The Effect of Interference Fit", Journal of Biomechanics, 41(3), 587-594.

Adam, F., Hammer, D. S., Pfautsch, S., Westermann, K., 2002, "Early Failure of a Press-Fit Carbon Fiber Hip Prosthesis with a Smooth Surface", The Journal of Arthroplasty, 17(2), 217-223.

Andrews, E., Gioux, G., Onck, P., Gibson, L., 2001, "Size Effects in Ductile Cellular Solids. Part Ii: Experimental Results", International Journal of Mechanical Sciences, 43(3), 701-713.

Austman, R. L., Milner, J. S., Holdsworth, D. W., Dunning, C. E., 2008, "The Effect of the Density-Modulus Relationship Selected to Apply Material Properties in a Finite Element Model of Long Bone", Journal of Biomechanics, 41, 3171-3176.

Baca, V., Horak, Z., Mikulenka, P., Dzupa, V., 2008, "Comparison of an Inhomogeneous Orthotropic and Isotropic Material Models Used for FE analyses", Medical Engineering & Physics, 30, 924-930.

Baleani, M., Cristofolini, L., Viceconti, M., 1999, "Endurance Testing of Hip Prostheses: A Comparison Between the Load Fixed in ISO 7206 Standard and the Physiological Loads", Clinical Biomechanics, 14, 339-345.

Behrens, B., Wirth, C., Windhagen, H., Nolte, I., Meyer-Lindenberg, A., Bouguecha, A., 2008, "Numerical Investigations of Stress Shielding in Total Hip Prostheses", Proceedings of the Institution of Mechanical Engineers, Part H: Journal of Engineering in Medicine, 222, 593-600.

Bendsøe, M. P., Kikuchi, N., 1988, "Generating Optimal Topologies in Structural Design Using a Homogenization Method", Computer Methods in Applied Mechanics and Engineering, 71, 197-224.

Bendsøe, M. P., Sigmund, O., 2003, "Topology Optimization: Theory, Methods, and Applications", Springer Verlag, Berlin, Heidelberd, New York.

Bidanda, B., Bártolo, P., 2008, Virtual Prototyping & Bio Manufacturing in Medical Applications, Springer Verlag, Chapter 5.

Bobyn, J., Stackpool, G., Hacking, S., Tanzer, M., Krygier, J., 1999, "Characteristics of Bone Ingrowth and Interface Mechanics of a New Porous Tantalum Biomaterial", Journal of Bone & Joint Surgery, British Volume, 81(5), 907.

Bobyn, J. D., Poggie, R., Krygier, J., Lewallen, D., Hanssen, A., Lewis, R., Unger, A., O'Keefe, T., Christie, M., Nasser, S., 2004, "Clinical Validation of a Structural Porous Tantalum Biomaterial for Adult Reconstruction", The Journal of Bone and Joint Surgery, 86, 123-129.

Boyle, C., Kim, I. Y., 2011, "Comparison of Different Hip Prosthesis Shapes Considering Micro-Level Bone Remodeling and Stress-Shielding Criteria Using Three-Dimensional Design Space Topology Optimization", Journal of Biomechanics, 44(9), 1722-1728.

Boyle, C., Kim, I. Y., 2011, "Three-Dimensional Micro-Level Computational Study of Wolff's Law Via Trabecular Bone Remodeling in the Human Proximal Femur Using Design Space Topology Optimization", Journal of Biomechanics, 44(5), 935-942.

Bragdon, C., Jasty, M., Greene, M., Rubash, H., Harris, W., 2004, "Biologic Fixation of Total Hip Implants: Insights Gained from a Series of Canine Studies", The Journal of Bone and Joint Surgery, 86, 105-117.

Carter, D., Orr, T., Fyhrie, D., 1989, "Relationships Between Loading History and Femoral Cancellous Bone Architecture", Journal of Biomechanics, 22, 231-244.

Cheah, C., Chua, C., Leong, K., Chua, S., 2003, "Development of a Tissue Engineering Scaffold Structure Library for Rapid Prototyping. Part 2: Parametric Library and Assembly Program", The International Journal of Advanced Manufacturing Technology, 21(4), 302-312.

Cheah, C., Chua, C., Leong, K., Chua, S., 2003, "Development of a Tissue Engineering Scaffold Structure Library for Rapid Prototyping. Part 1: Investigation and Classification", The International Journal of Advanced Manufacturing Technology, 21(4), 291-301.

Chen, J., Huang, M., 1998, "Fracture Analysis of Cellular Materials: A Strain Gradient Model", Journal of the Mechanics and Physics of Solids, 46(5), 789-828.

Christensen, R. M., 2000, "Mechanics of Cellular and Other Low-Density Materials", International Journal of Solids and Structures, 37(1-2), 93-104.

Chu, T. M. G., Orton, D. G., Hollister, S. J., Feinberg, S. E., Halloran, J. W., 2002, "Mechanical and In Vivo Performance of Hydroxyapatite Implants with Controlled Architectures", Biomaterials, 23, 1283-1293.

Coelho, P., Fernandes, P., Guedes, J., Rodrigues, H., 2008, "A Hierarchical Model for Concurrent Material and Topology Optimisation of Three-Dimensional Structures", Structural and Multidisciplinary Optimization, 35(2), 107-115.

Coelho, P. G., Cardoso, J. B., Fernandes, P. R., Rodrigues, H. C., 2011, "Parallel Computing Techniques Applied to the Simultaneous Design of Structure and Material", Advances in Engineering Software, 42, 219-227.

Cote, F., Deshpande, V., Fleck, N., Evans, A., 2006, "The Compressive and Shear Responses of Corrugated and Diamond Lattice Materials", International Journal of Solids and Structures, 43, 6220-6242.

Côté, F., Deshpande, V. S., Fleck, N. A., 2007a, "Shear Fatigue Strength of a Prismatic Diamond Sandwich Core", Scripta Materialia, 56, 585-588.

Côté, F., Fleck, N. A., Deshpande, V. S., 2007b, "Fatigue Performance of Sandwich Beams with a Pyramidal Core", International Journal of Fatigue, 29, 1402-1412.

Deb, K., Pratap, A., Agarwal, S., Meyarivan, T., 2002, "A Fast and Elitist Multiobjective Genetic Algorithm: NSGA-II", IEEE Transactions on Evolutionary Computation, 6, 182-197.

Diaaz, A., Kikuchi, N., 1992, "Solutions to Shape and Topology Eigenvalue Optimization Problems Using a Homogenization Method", International Journal for Numerical Methods in Engineering, 35, 1487-1502.

Dumontet, H., 1986, "Study of a Boundary Layer Problem in Elastic Composite Materials", RAIRO Model. Math. Anal., Numér 20, 265-286.

Fang, Z., Starly, B., Sun, W., 2005, "Computer-Aided Characterization for Effective Mechanical Properties of Porous Tissue Scaffolds", Computer-Aided Design, 37(1), 65-72.

Fraldi, M., Esposito, L., Perrella, G., Cutolo A., Cowin, S., 2010, "Topological Optimization in Hip Prosthesis Design", Biomechanics and modeling in mechanobiology, 9(4), 389-402.

Ghosh, S., Lee, K., Raghavan, P., 2001, "A Multi-Level Computational Model for Multi-Scale Damage Analysis in Composite and Porous Materials", International Journal of Solids and Structures, 38, 2335-2385.

Gibson, L., Ashby, M., 1999, *Cellular Solids: Structure and Properties*, Cambridge University Press.

Gibson, L. J., 2005, "Biomechanics of Cellular Solids", Journal of Biomechanics, 38, 377-399.

Glassman, A., Bobyn, J., Tanzer, M., 2006, "New Femoral Designs Do They Influence Stress Shielding?", Clinical Orthopaedics and Related Research, 453, 64-74.

Gonøalves Coelho, P., Rui Fernandes, P., Carrico Rodrigues, H., 2011, "Multiscale Modeling of Bone Tissue with Surface and Permeability Control", Journal of Biomechanics, 44, 321-329.

Grübl, A., Marker, M., Brodner, W., Giurea, A., Heinze, G., Meisinger, V., Zehetgruber, H. Kotz, R., 2007, "Long Term Follow up of Metal on Metal Total Hip Replacement", Journal of Orthopaedic Research, 25(7), 841-848.

Guedes, J., Kikuchi, N., 1990, "Preprocessing and Postprocessing for Materials Based on the Homogenization Method with Adaptive Finite Element Method", Computer Methods in Applied Mechanics and Engineering, 83, 143-198.

Harrysson, O. L. A., Cansizoglu, O., Marcellin-Little, D. J., Cormier, D. R., West li, H. A., 2008, "Direct Metal Fabrication of Titanium Implants with Tailored Materials and Mechanical Properties using Electron Beam Melting Technology", Materials Science and Engineering: C 28, 366-373.

Harvey, E., Bobyn, J., Tanzer, M., Stackpool, G., Krygier, J., Hacking, S., 1999, "Effect of Flexibility of the Femoral Stem on Bone-Remodeling and Fixation of the Stem in a Canine Total Hip Arthroplasty Model without Cement", The Journal of Bone and Joint Surgery, 81(1), 93.

Hassani, B., 1996, "A Direct Method to Derive the Boundary Conditions of the Homogenization Equation for Symmetric Cells", Communications in Numerical Methods in Engineering, 12, 185-196.

Hassani, B., Hinton, E., 1998, "A Review of Homogenization and Topology Optimization I—Homogenization Theory for Media with Periodic Structure", Computers & Structures, 69(6), 707-717.

Hassani, B., Hinton, E., 1998, "A Review of Homogenization and Topology Opimization Ii—Analytical and Numerical Solution of Homogenization Equations", Computers & Structures, 69(6), 719-738.

Hassani, B., Hinton, E., 1998, "A Review of Homogenization and Topology Optimization I I I—Topology Optimization Using Optimality Criteria", Computers & Structures, 69 (6), 739-756.

Hedia, H., Barton, D., Fisher, J., Elmidany, T., 1996, "A Method for Shape Optimization of a Hip Prosthesis to Maximize the Fatigue Life of the Cement", Medical Engineering & Physics, 18, 647-654.

Hedia, H., Shabara, M., El-Midany, T., Fouda, N., 2006, "Improved Design of Cementless Hip Stems Using Two-Dimensional Functionally Graded Materials", Journal of Biomedical Materials Research Part B: Applied Biomaterials, 79(1), 42-49.

Hedia, H. S., Mahmoud, N.-A., 2004, "Design Optimization of Functionally Graded Dental Implant", Bio-Medical Materials & Engineering, 14(2), 133-143.

Heinl, P., Müller, L., Körner, C., Singer, R. F., Müller, F. A., 2008, "Cellular Ti-6al-4v Structures with Interconnected Macro Porosity for Bone Implants Fabricated by Selective Electron Beam Melting", Acta Biomaterialia, 4(5), 1536-1544.

Hoffman, O., 1967, "The Brittle Strength of Orthotropic Material", Journal of Composite Materials, 1(3), 200-206.

Hollister, S., Kikuchi, N., 1992, "A Comparison of Homogenization and Standard Mechanics Analyses for Periodic Porous Composites", Computational Mechanics, 10, 73-95.

Hollister, S. J., 2005, "Porous Scaffold Design for Tissue Engineering", Nature Materials, 4, 518-524.

Hollister, S. J., Lin, C. Y., Kang, H., Adachi, T., 2008, "Computational Design and Simulation of Tissue Engineering Scaffolds", Virtual Prototyping & Bio Manufacturing in Medical Applications, 113-127.

Huang, J. S., Lin, J. Y., 1996, "Fatigue of Cellular Materials", Acta Materialia, 44, 289-296.

Huang, J.-S., Liu, S.-Y., 2001a, "Fatigue of Honeycombs Under In-Plane Multiaxial Loads", Materials Science and Engineering: A, 308, 45-52.

Huang, J.-S., Liu, S.-Y., 2001b, "Fatigue of Isotropic Open-Cell Foams Under Multiaxial Loads", International Journal of Fatigue, 23, 233-240.

Huiskes, R., Weinans, H., Grootenboer, H. J., Dalstra, M., Fudala, B., Slooff, T. J., 1987, "Adaptive Bone-Remodeling Theory Applied to Prosthetic-Design Analysis", Journal of Biomechanics, 20, 1135-1150.

Huiskes, R., Weinans, H., Rietbergen, B., 1992, "The Relationship between Stress Shielding and Bone Resorption around Total Hip Stems and the Effects of Flexible Materials", Clinical Orthopaedics and Related Research, 274, 124-134.

Kalamkarov, A. L., Andrianov, I. V., Danishevs'kyy, V. V., 2009, "Asymptotic Homogenization of Composite Materials and Structures", Applied Mechanics Reviews, 62, 030802.

Kang, H., Lin, C. Y., Hollister, S. J., 2010, "Topology Optimization of Three Dimensional Tissue Engineering Scaffold Architectures for Prescribed Bulk Modulus and Diffusivity", Structural and Multidisciplinary Optimization, 42, 633-644.

Kanouté, P., Boso, D., Chaboche, J., Schrefler, B., 2009, "Multiscale Methods for Composites: A Review", Archives of Computational Methods in Engineering, 16, 31-75.

Katti, K. S., 2004, "Biomaterials in Total Joint Replacement", Colloids and Surfaces B: Biointerfaces, 39(3), 133-142.

Kayabasi, O., Ekici, B., 2007, "The Effects of Static, Dynamic and Fatigue Behavior on Three-Dimensional Shape Optimization of Hip Prosthesis by Finite Element Method", Materials & Design, 28, 2269-2277.

Khanoki, S. A., Pasini, D., 2012, "Multiscale Design and Multiobjective Optimization of Orthopedic Hip Implants with Functionally Graded Cellular Material", Journal of Biomechanical Engineering, 134, 031004.

Kobayashi, S., Saito, N., Horiuchi, H., Iorio, R., Takaoka, K., 2000, "Poor Bone Quality or Hip Structure as Risk Factors Affecting Survival of Total-Hip Arthroplasty", The Lancet, 355(9214), 1499-1504.

Kowalczyk, P., 2001, "Design Optimization of Cementless Femoral Hip Prostheses Using Finite Element Analysis", Journal of Biomechanical Engineering, 123(5), 396-402.

Kruch, S., 2007, "Homogenized and Relocalized Mechanical Fields", The Journal of Strain Analysis for Engineering Design, 42(4), 215-226.

Kuiper, J., Huiskes, R., 1992, "Numerical Optimization of Hip-Prosthetic Stem Material", Recent Advances in Computer Methods in Biomechanics & Biomedical Engineering. J. Middleton, G N Pande, and K R Williams, 76-84.

Kuiper, J., Huiskes, R., 1996, "Friction and Stem Stiffness Affect Dynamic Interface Motion in Total Hip Replacement", Journal of Orthopaedic Research, 14, 36-43.

Kuiper, J., Huiskes, R., 1997, "Mathematical Optimization of Elastic Properties: Application to Cementless Hip Stem Design", Transactions-American Society of Mechanical Engineers Journal of Biomechanical Engineering, 119, 166-174.

Kumar, R., McDowell, D., 2004, "Generalized Continuum Modeling of 2-D Periodic Cellular Solids", International Journal of Solids and Structures, 41(26), 7399-7422.

Kurtz, S., Gawel, H., Patel, J., 2011, "History and Systematic Review of Wear and Osteolysis Outcomes for First-Generation Highly Crosslinked Polyethylene", Clinical Orthopaedics and Related Research, 469(8), 2262-2277.

Kurtz, S., Ong, K., Lau, E., Mowat, F., Halpern, M., 2007, "Projections of Primary and Revision Hip and Knee Arthroplasty in the United States from 2005 to 2030", The Journal of Bone and Joint Surgery, 89(4), 780.

Lefik, M., Schrefler, B., 1996, "Fe Modelling of a Boundary Layer Corrector for Composites Using the Homogenization Theory", Engineering Computations, 13(6), 31-42.

Li, C., Granger, C., Schutte, H. D., Biggers, S. B., Kennedy, J. M., Latour, R. A., 2002, "Progressive Failure Analysis of Laminated Composite Femoral Prostheses for Total Hip Arthroplasty", Biomaterials, 23, 4249-4262.

Li, S. J., Murr, L. E., Cheng, X. Y., Zhang, Z. B., Hao, Y. L., Yang, R., Medina, F., Wicker, R. B., 2012, "Compression Fatigue Behavior of Ti-6A1-4V Mesh Arrays Fabricated by Electron Beam Melting", Acta Materialia, 60, 793-802.

Lin, C. Y., Kikuchi, N., Hollister, S. J., 2004, "A Novel Method for Biomaterial Scaffold Internal Architecture Design to Match Bone Elastic Properties with Desired Porosity", Journal of Biomechanics, 37, 623-636.

Liu, P. S., Du, H. Y., 2011, "Modeling Failure Modes of Isotropic Three-Dimensional Reticulated Porous Metal Foams Under Several Typical Loads", Materials & Design 32, 4786-4793.

Masters, I., Evans, K., 1996, "Models for the Elastic Deformation of Honeycombs", Composite Structures, 35(4), 403-422.

Matsui, K., Terada, K., Yuge, K., 2004, "Two-Scale Finite Element Analysis of Heterogeneous Solids with Periodic Microstructures", Computers & Structures, 82(7-8), 593-606.

Moen, T. C., Ghate, R., Salaz, N., Ghodasra, J., Stulberg, S. D., 2011, "A Monoblock Porous Tantalum Acetabular Cup Has No Osteolysis on Ct at 10 Years", Clinical orthopaedics and related research, 469(2), 382-386.

Murr, L., Gaytan, S., Medina, F., Lopez, H., Martinez, E., Machado, B., Hernandez, D., Martinez, L., Lopez, M., Wicker, R., 2010, "Next-Generation Biomedical Implants Using Additive Manufacturing of Complex, Cellular and Functional Mesh Arrays", Philosophical Transactions of the Royal Society A: Mathematical, Physical and Engineering Sciences, 368(1917), 1999-2032.

Murr, L. E., Quinones, S. A., Gaytan, S. M., Lopez, M. I., Rodela, A., Martinez, E. Y., Hernandez, D. H., Martinez, E., Medina, F., Wicker, R. B., 2009, "Microstructure and Mechanical Behavior of Ti-6Al-4V Produced by Rapid-Layer Manufacturing, for Biomedical Applications", Journal of the Mechanical Behavior of Biomedical Materials, 2, 20-32.

Neumann, D. R. P., Thaler, C., Hitzl, W., Huber, M., Hofstadter, T., Dorn, U., 2010, "Long-Term Results of a Contemporary Metal-on-Metal Total Hip Arthroplasty: A 10-Year Follow-up Study", The Journal of Arthroplasty, 25(5), 700-708.

Nganbe, M., Khan, U., Louati, H., Speirs, A., Beaule, P. E., 2011, "In Vitro Assessment of Strength, Fatigue Durability, and Disassembly of Ti6Al4V and CoCrMo Necks in Modular Total Hip Replacements", Journal of Biomedical Materials Research Part B: Applied Biomaterials, 97B, 132-138.

Objet-Geometries, I., 2011. Objet Inc, Billerica, US.

Olurin, O., McCullough, K., Fleck, N., Ashby, M., 2001, "Fatigue Crack Propagation in Aluminium Alloy Foams", International Journal of Fatigue, 23, 375-382.

Pal, B., Gupta, S., New, A., 2009, "A Numerical Study of Failure Mechanisms in the Cemented Resurfaced Femur: Effects of Interface Characteristics and Bone Remodelling", Proceedings of the Institution of Mechanical Engineers, Part H: Journal of Engineering in Medicine, 223(4), 471-484.

Parthasarathy, J., Starly, B., Raman, S., Christensen, A., 2010, "Mechanical Evaluation of Porous Titanium (Ti6al4v) Structures with Electron Beam Melting (Ebm)", Journal of the Mechanical Behavior of Biomedical Materials, 3(3), 249-259.

Pellegrino, C., Galvanetto, U., Schrefler, B., 1999, "Numerical Homogenization of Periodic Composite Materials with Non Linear Material Components", International Journal for Numerical Methods in Engineering, 46(10), 1609-1637.

Peng, L., Bai, J., Zeng, X., Zhou, Y., 2006, "Comparison of Isotropic and Orthotropic Material Property Assignments on Femoral Finite Element Models Under Two Loading Conditions", Medical Engineering & Physics, 28, 227-233.

Pérez, M., Fornells, P., Doblare, M., Garcia-Aznar, J., 2010, "Comparative Analysis of Bone Remodelling Models with Respect to Computerised Tomography-Based Finite Element Models of Bone", Computer Methods in Biomechanics and Biomedical Engineering, 13, 71-80.

Pettersen, S. H., Wik, T. S., Skallerud, B., 2009, "Subject Specific Finite Element Analysis of Stress Shielding Around a Cementless Femoral Stem", Clinical Biomechanics, 24, 196-202.

Ploeg, H.-L., Bürgi, M., Wyss, U. P., 2009, "Hip Stem Fatigue Test Prediction", International Journal of Fatigue, 31, 894-905.

Raghavan, P., Ghosh, S., 2004, "Concurrent Multi-Scale Analysis of Elastic Composites by a Multi-Level Computational Model", Computer Methods in Applied Mechanics and Engineering, 193, 497-538.

Raimondi, M., Pietrabissa, R., 1999, "Modelling Evaluation of the Testing Condition Influence on the Maximum Stress Induced in a Hip Prosthesis During ISO 7206 Fatigue Testing", Medical Engineering & Physics, 21, 353-359.

Reilly, G. C., Engler, A. J., 2010, "Intrinsic Extracellular Matrix Properties Regulate Stem Cell Differentiation", Journal of Biomechanics, 43, 55-62.

Rodrigues, H., Guedes, J., Bendsøe, M., 2002, "Hierarchical Optimization of Material and Structure", Structural and Multidisciplinary Optimization, 24(1), 1-10.

Senalp, A. Z., Kayabasi, O., Kurtaran, H., 2007, "Static, Dynamic and Fatigue Behavior of Newly Designed Stem Shapes for Hip Prosthesis Using Finite Element Analysis", Materials & Design, 28, 1577-1583.

Sevilla, P., Aparicio, C., Planell, J. A., Gil, F. J., 2007, "Comparison of the Mechanical Properties Between Tantalum and Nickel-Titanium Foams Implant Materials for Bone Ingrowth Applications", Journal of Alloys and Compounds, 439, 67-73.

Simone, A., Gibson, L., 1998, "Effects of Solid Distribution on the Stiffness and Strength of Metallic Foams", Acta Materialia, 46(6), 2139-2150.

Stamp, R., Fox, P., O'Neill, W., Jones, E., Sutcliffe, C., 2009, "The Development of a Scanning Strategy for the Manufacture of Porous Biomaterials by Selective Laser Melting", Journal of Materials Science: Materials in Medicine, 20(9), 1839-1848.

Suzuki, K., Kikuchi, N., 1991, "A Homogenization Method for Shape and Topology Optimization", Computer methods in Applied Mechanics and Engineering, 93(3), 291-318.

Takano, N., Zako, M., Okuno, Y., 2003, "Multi-Scale Finite Element Analysis of Porous Materials and Components by Asymptotic Homogenization Theory and Enhanced Mesh Superposition Method", Modelling and Simulation in Materials Science and Engineering, 11, 137-156.

Thompson, I., Hench, L., 1998, "Mechanical Properties of Bioactive Glasses, Glass-Ceramics and Composites", Proceedings of the Institution of Mechanical Engineers, Part H: Journal of Engineering in Medicine, 212(2), 127.

Trebse, R., Milosev, I., Kovac, S., Mikek, M., Pisot, V., 2005, "Poor Results from the Isoelastic Total Hip Replacement", Acta Orthopaedica, 76(2), 169-176.

Van Bael, S., Chai, Y. C., Truscello, S., Moesen, M., Kerckhofs, G., Van Oosterwyck, H., Kruth, J. P., Schrooten, J., 2012, "The Effect of Pore Geometry on the In Vitro Biological Behavior of Human Periosteum-Derived Cells Seeded on Selective Laser-Melted Ti6Al4V Bone Scaffolds", Acta Biomaterialia, 8, 2824-2834.

Viceconti, M., Brusi, G., Pancanti, A., Cristofolini, L., 2006, "Primary Stability of an Anatomical Cementless Hip Stem: A Statistical Analysis", Journal of Biomechanics, 39(7), 1169-1179.

Viceconti, M., Monti, L., Muccini, R., Bernakiewicz, M., Toni, A., 2001, "Even a Thin Layer of Soft Tissue May Compromise the Primary Stability of Cementless Hip Stems", Clinical Biomechanics, 16(9), 765-775.

Viceconti, M., Muccini, R., Bernakiewicz, M., Baleani, M., Cristofolini, L., 2000, "Large-Sliding Contact Elements Accurately Predict Levels of Bone-Implant Micromotion Relevant to Osseointegration", Journal of Biomechanics, 33(12), 1611-1618.

Vichinsky, E. P., Neumayr, L. D., Haberkern, C., Earles, A. N., Eckman, J., Koshy, M., Black, D. M., 1999, "The Perioperative Complication Rate of Orthopedic Surgery in Sickle Cell Disease: Report of the National Sickle Cell Surgery Study Group", American journal of hematology, 62(3), 129-138.

Vigliotti, A., Pasini, D., 2012, "Stiffness and Strength of Tridimensional Periodic Lattices", Computer Methods in Applied Mechanics and Engineering, 229-232, 27-43.

Wang, A., McDowell, D., 2004, "In-Plane Stiffness and Yield Strength of Periodic Metal Honeycombs", Journal of Engineering Materials and Technology, 126, 137-156.

Wang, H. V., 2005, "A Unit Cell Approach for Lightweight Structure and Compliant Mechanism", Ph.D. thesis, Georgia Institute Of Technology.

Wang, W.-X., Luo, D., Takao, Y., Kakimoto, K., 2006, "New Solution Method for Homogenization Analysis and Its Application to the Prediction of Macroscopic Elastic Constants of Materials with Periodic Microstructures", Computers & Structures, 84(15-16), 991-1001.

Warren, W., Byskov, E., 2002, "Three-Fold Symmetry Restrictions on Two-Dimensional Micropolar Materials", European Journal of Mechanics-A/Solids, 21(5), 779-792.

Watari, F., Yokoyama, A., Saso, F., Uo, M., Kawasaki, T., 1997, "Fabrication and Properties of Functionally Graded Dental Implant", Composites Part B: Engineering, 28(1-2), 5-11.

Weinans, H., Huiskes, R., Grootenboer, H., 1992, "Effects of Material Properties of Femoral Hip Components on Bone Remodeling", Journal of Orthopaedic Research, 10(6), 845-853.

Weinans, H., Huiskes, R., Grootenboer, H. J., 1992, "The Behavior of Adaptive Bone-Remodeling Simulation Models", Journal of Biomechanics, 25(12), 1425-1441.

Yang, S., Leong, K., Du, Z., Chua, C., 2002, "The Design of Scaffolds for Use in Tissue Engineering. Part Ii. Rapid Prototyping Techniques", Tissue Engineering, 8(1), 1-11.

Yuan, F., Pagano, N., 2003, "Size Scales for Accurate Homogenization in the Presence of Severe Stress Gradients", Mechanics of Advanced Materials and Structures, 10, 353-365.

Zardiackas, L. D., Parsell, D. E., Dillon, L. D., Mitchell, D. W., Nunnery, L. A., Poggie, R., 2001, "Structure, Metallurgy, and Mechanical Properties of a Porous Tantalum Foam", Journal of Biomedical Materials Research, 58, 180-187.

Zhou, J., Soboyejo, W. O., 2004, "Compression—Compression Fatigue of Open Cell Aluminum Foams: Macro-/Micro-Mechanisms and the Effects of Heat Treatment", Materials Science and Engineering: A, 369, 23-35.

Zienkiewicz, O. C., Taylor, R. L., 2005, The Finite Element Method for Solid and Structural Mechanics, Butterworth-Heinemann.

What is claimed is:

1. A method for producing a prosthetic graded cellular bone implant having non-homogeneous distribution of material properties comprising the steps of:
   generating a finite element model of the implant comprising a plurality of unit cells defining a lattice microstructure;
   calculating a homogenized stiffness tensor for each unit cell;
   determining a homogenous medium for each unit cell having an equivalent homogenized stiffness tensor;
   determining strains and stresses on the implant using either the homogenized stiffness tensors or a finite element analysis;
   generating a stress field for each unit cell using a stress recovery procedure conducted on the determined strains and stresses;
   determining if the stress field of each unit cell is below a predefined failure criterion, and if so, performing a multiobjective optimization to minimize bone loss and interface failure by optimizing at least one constraint including average porosity, mean pore size and cell wall thickness for each unit cell;
   generating a model of the graded cellular implant combining the optimized stress field of each unit cell; and
   producing the prosthetic graded cellular bone implant from the model of the graded cellular implant.

2. The method of claim 1, wherein the bone implant is a hip implant, a knee implant, an elbow implant, a shoulder implant, a wrist implant, an ankle implant, or a dental implant.

3. The method of claim 1, wherein the porosity of the implant is greater than or equal to 40%.

4. The method of claim 1, wherein the mean pore size of the implant is between 50 μm and 800 μm.

5. The method of claim 1, wherein the cell wall thickness of each unit cell is between 70 μm and 100 μm.

6. The method of claim 1, further comprising forming the cell wall thickness of each unit cell to be between 70 μm and a size where the cell wall completely fills a pore of the unit cell.

7. The method of claim 3, further comprising forming the porosity of the implant to be between 60% and 95%.

8. The method of claim 1, comprising conducting an analysis of the lattice microstructure to individually model each strut of each unit cell.

9. The method of claim 8, wherein conducting the analysis of the lattice microstructure to individually model each strut of each unit cell is performed as an alternative to calculating the homogenized stiffness tensor for each unit cell.

10. The method of claim 8, comprising using stiffness properties for each unit cell obtained from the analysis of the lattice microstructure.

11. The method of claim 10, wherein using the stiffness properties is performed as an alternative to determining a homogenous medium for each unit cell having the equivalent homogenized stiffness tensor.

12. The method of claim 1, wherein performing the multiobjective optimization includes performing the multiobjective optimization with either a gradient-based or a gradient-free optimization algorithm.

13. The method of claim 1, wherein the non-homogenous material properties include at least one of: strength, osteoconductivity, pore geometry, porosity, and surface roughness.

14. The method of claim 13, wherein:
   the properties includes the strength of the lattice microstructure; and
   the cell topology of unit cells of the plurality of unit cells comprised by a portion of the lattice microstructure being selected to be open or closed to grade the strength of the portion of the lattice microstructure.

15. The method of claim 13, wherein:
   the properties includes the osteoconductivity of the lattice microstructure; and the cell topology of unit cells of the plurality of unit cells comprised by a portion of the lattice microstructure being selected to be open or closed to grade the osteoconductivity of the portion of the lattice microstructure.

16. The method of claim 13, wherein the properties include the surface roughness;
the surface roughness being graded between surface roughness values of between 0.5 micron and 8.5 micron.

17. The method of claim 4, further comprising forming the mean pore size range to be between 200 micron and 400 micron.

18. The method of claim 7, wherein the porosity of the implant is between 70% and 90%.

19. The method of claim 1, wherein the implant is one of a hip implant, a knee implant, an elbow implant, a wrist implant, a shoulder implant, an ankle implant or a dental implant.

* * * * *